(12) United States Patent
Weed et al.

(10) Patent No.: US 9,114,313 B2
(45) Date of Patent: Aug. 25, 2015

(54) PUZZLE BOARD GAME

(71) Applicants: Terry Alan Weed, Costa Mesa, CA (US); Amy Marie Hathaway, Mission Viejo, CA (US)

(72) Inventors: Terry Alan Weed, Costa Mesa, CA (US); Amy Marie Hathaway, Mission Viejo, CA (US)

( * ) Notice: Subject to any disclaimer, the term of this patent is extended or adjusted under 35 U.S.C. 154(b) by 87 days.

(21) Appl. No.: 13/952,598

(22) Filed: Jul. 27, 2013

(65) Prior Publication Data
US 2014/0206423 A1    Jul. 24, 2014

Related U.S. Application Data

(60) Provisional application No. 61/694,257, filed on Aug. 29, 2012.

(51) Int. Cl.
| | |
|---|---|
| *A63F 9/06* | (2006.01) |
| *A63F 3/04* | (2006.01) |
| *A63F 9/10* | (2006.01) |
| *G09B 1/36* | (2006.01) |
| *G09B 19/00* | (2006.01) |

(52) U.S. Cl.
CPC ............ *A63F 9/0612* (2013.01); *A63F 3/0478* (2013.01); *A63F 9/10* (2013.01); *G09B 1/36* (2013.01); *G09B 19/00* (2013.01); *G09B 19/0092* (2013.01); *A63F 2003/0486* (2013.01); *A63F 2003/0492* (2013.01); *A63F 2009/105* (2013.01); *A63F 2009/1066* (2013.01)

(58) Field of Classification Search
CPC ....... A63F 9/0612; A63F 9/10; A63F 9/1011; A63F 3/0478

USPC .................... 273/153 R, 154–156, 157 R
See application file for complete search history.

(56) References Cited

U.S. PATENT DOCUMENTS

| | | | | |
|---|---|---|---|---|
| 2,199,499 | A * | 5/1940 | Kreitler | 273/273 |
| 4,669,734 | A * | 6/1987 | Watkins | 273/157 R |
| 4,792,138 | A * | 12/1988 | Watkins | 273/157 R |
| 4,961,708 | A * | 10/1990 | Van Niekerk | 434/406 |
| 5,149,098 | A * | 9/1992 | Bianchi | 273/157 R |
| 5,362,054 | A * | 11/1994 | Ashemimry | 273/157 R |
| 6,425,581 | B1 * | 7/2002 | Barrett | 273/157 R |
| 8,308,537 | B2 * | 11/2012 | Sherin et al. | 463/9 |
| 8,573,596 | B2 * | 11/2013 | Gearty | 273/157 R |
| 2005/0093232 | A1 * | 5/2005 | Stout | 273/153 R |
| 2013/0079079 | A1 * | 3/2013 | Bouchard et al. | 463/9 |
| 2013/0328265 | A1 * | 12/2013 | Wu | 273/157 R |

* cited by examiner

*Primary Examiner* — Jay Liddle
*Assistant Examiner* — Alex F. R. P. Rada, II

(57) ABSTRACT

A puzzle game system, similar to a jigsaw puzzle, can be played by a single player or by multiple players. The game system has a game board having a multiplicity of game board locations. One, of multiple puzzle pieces, is placed into each game board location. In one embodiment, the game board locations combine to form the shape of a human body and the puzzle pieces represent diet choices. At the end of the game, each player is scored based on the health and wellness achieved by the selected puzzle piece. A scoring system conceals the results until the game ends. For example, scoring features may be present on the backs of the puzzle pieces, and at the end of the game, each player can turn over their game board and obtain a score based on the scoring features seen through openings in the back of the game board.

11 Claims, 19 Drawing Sheets

Frequency Table

PUZZLE BOARD GAME

CROSS REFERENCE TO RELATED PATENTS

This application claims the benefit of provisional patent application No. 61/694,157, EFS ID 13611210, confirmation number 5749 for "Puzzle Board Game" filed on Aug. 29, 2012 by the present inventors which is incorporated by reference.

BACKGROUND

Prior Art

U.S. Patents

| Patent Number | Issue Date | Patentee |
| --- | --- | --- |
| U.S. patents | | |
| U.S. Pat. No. 3,558,136, | Jan. 26, 1971 | McFarland |
| U.S. Pat. No. 4,052,072 | Oct. 4, 1977 | Beal |
| U.S. Pat. No. 3,542,368, | Nov. 24, 1979 | Ashley |
| U.S. Pat. No. 4,219,194 A | Aug. 26, 1980 | Powers |
| U.S. Pat. No. 4,792,138 | Dec. 20, 1988 | Watkins |
| U.S. Pat. No. 5,062,637 | Nov. 5, 1991 | Bianchi |
| U.S. Pat. No. 5,643,084 | Jul. 1, 1997 | Mirsky |
| U.S. Pat. No. 6,193,234 | Feb. 27, 2002 | Jones |
| Foreign Patent Documents | | |
| WO-1986004513-A1 | 1986 Aug. 14 | Watkins |
| AU2007100179 (A4) | 2008 Sep. 18 | Cocis |

Various forms of board games have been devised over the years. Also, numerous forms of jigsaw puzzles have been created. Board games are games typically played by two or more people. On the other hand, a jigsaw puzzle is typically assembled by a single person. Both board games and jigsaw puzzles present challenges to those who play them. Each may vary from the very simple to the incredibly complex. Each can provide minutes and hours of fun, enjoyment, and intrigue. But the attributes and capabilities associated with each has never been combined into a useful and fun puzzle game where two or more players can compete against each from a common pool of puzzle pieces where each individual puzzle piece has more than one individual score attached to it and two or more puzzle pieces compete for the same puzzle coordinate. Further, there is no jigsaw puzzle or jigsaw puzzle game in existence where the scores are displayed from the back side of each puzzle piece through holes in the back of the jigsaw puzzle board. In addition, no other jigsaw puzzle game offers an outcome with more than one score with a single play of the game. Also, no other jigsaw puzzle game provides for the capability of offering an index that allows the players to correlate the scores from the game to other pertinent data that is related to the game, such as, but not limited to, correlating the game scores to human biometrics such as human body weight change, blood cholesterol level change, blood pressure change, blood glucose level change and the like. Additionally, no previous games allow for the score outcome to be related to such an index which can then be correlated directly to the player's personal biometrics, such as, but not limited to weight change, blood cholesterol level change, blood pressure change, glucose level change and the like.

Several patents exist that disclose puzzle games involving two or more players competing to complete a puzzle. For example, U.S. Pat. No. 3,558,136, issued on Jan. 26, 1971 to McFarland discloses a jigsaw puzzle game played by two opposing players or teams, each having identically cut and illustrated, but differently colored, pieces of a scene. Similarly, U.S. Pat. No. 5,062,637, issued on Nov. 5, 1991 to Bianchi discloses a method of playing a jigsaw board game with two players, wherein each player has a board, and all game pieces are piled on a playing table. However, neither patent discloses using puzzle pieces that have an individual score attached to each puzzle piece that can result in more than one score for each game play and for each player. Further, U.S. Pat. No. 5,062,637 does not disclose a method of scoring for measuring a player's performance in placing puzzle pieces.

Many other types of jigsaw puzzle games have been proposed in previous years, such as U.S. Pat. No. 4,052,072 by Beal (1977). Beal's game is an educational world map game adapted to be played on a pachisi-like game playing board bearing the world continental areas with countries marked off and lines of playing spaces to be traversed by playing pieces counted off in number according to the roll of dice and directed by a drawing of a card or playing piece showing the country shape in one of the continental areas. The game is completed with all of the countries provided for the continental areas being placed therein and the winner will be the player who has located the greater number of countries in the continental areas or scored the most points according to variations of the game. This game does not offer a multiple scoring system or an index to correlate the game score to additional multiple game data or factors or parameters or biometrics. Nor does this game offer the simple method of turning the jigsaw puzzle over to tally a player's score.

U.S. Pat. No. 4,792,138 to Watkins (1988) also shows a puzzle game for multiple players with a scoring system, however, the scoring system is based on filling certain areas of the puzzle in order to obtain the highest score and it uses score cards. This game does not offer a scoring system with holes or indicators on the back side of the puzzle nor does it offer more than one score for a single game play.

U.S. Pat. No. 6,193,234 to Jones (2001) also shows a puzzle game for multiple players with a scoring system, however, the scoring system includes a spinner in which the player must spin the spinner to randomly define how many inner puzzle pieces that player may take to complete an inner region of a puzzle. Afterwards, a stopwatch may be used to time how long the player takes to place as many inner puzzle pieces inside the puzzle frame as possible. After the player has completed an attempt at placing as many inner puzzle pieces as possible, the player's performance for the round is recorded on a score sheet for tracking that player's performance during the life of the game. This game does not offer a puzzle backboard with holes in it to enable the player to tally multiple scores nor does it provide for the score to correlate to an index.

There are other jigsaw games that have been proposed that have two identical jigsaw game boards for each player such as U.S. Pat. No. 4,219,194 to Powers. The object of the game with the Powers' game is for each player to win the game by being the player to assemble the most pieces of the common puzzle. Once again, there is no allowance for a numeric score or for multiple scores nor is there the capability to correlate the game scores to an index of pertinent data to the players.

Another jigsaw game scoring system was also proposed such as Patent Publication No. WO-1986004513-A1 to Watkins. Watkins offers a board game method of playing the game in which pieces of a jigsaw puzzle are assembled over particular indicia of a game board. Points are assigned based on covering or connecting certain areas of the game board and by playing a uniquely shaped piece of the puzzle in a particular manner. Score cards are assigned to players when points are earned, and totaled at the end of the game. Still this game offers only one set of points for each player and does not offer multiple score outcomes for each player. It also does not provide for the score indicators to be on the back of each puzzle piece to be displayed through holes in the back of the puzzle board.

There are also other educational jigsaw puzzle games that have been proposed such as Australian Patent AU2007100179 by Cocis. Cocis offers a jigsaw educational game with a plurality of jigsaw sheets or boards representing different geographical regions such as continents or islands of the world.

U.S. Pat. No. 5,643,084 by Mirsky offers a software version of a Jigsaw puzzle game. Mirsky's game does not offer any way to provide the players with a choice of having one or more scores for a single play session of the game.

All of the aforementioned prior art does not offer the novel feature of a jigsaw puzzle with holes or openings in the back board that allow for the scoring system to be tallied simply by turning over the jigsaw puzzle board. In addition, prior art does not allow for the players to have a choice of having just one score for their play of the game to determine the game winner or for having a choice to have a plurality of scores or a combination of only certain scores to determine the game winner. Additionally, prior art does not allow for the game score to correlate directly to one or more indices that offer more data of greater value to the players. In addition, prior art does not allow for data from the indices to be related to each individual player personally by means of a calculation device such as a slide rule, spreadsheet, software algorithm or another similar method of deriving a calculation. Therefore, none of the prior art, taken either singly or in combination, is seen to describe the embodiments as claimed herein.

SUMMARY OF THE INVENTION

The present invention addresses the above and other needs by providing a puzzle game system, similar to a jigsaw puzzle, which can be played by a single player or by multiple players. The game system has a game board having a multiplicity of game board locations and one of multiple of puzzle pieces are placed into each game board location. In one embodiment, the game board locations combine to form the shape of a human body and the puzzle pieces represent diet choices. At the end of the game, each player is scored based on the health and wellness achieved by the selected puzzle piece. A scoring system conceals the results until the end of the game. For example, scoring features may be present on the backs of the puzzle pieces, and the end of the game, each player can turn their game board and obtain a score based on the scoring features seen through opening in the back of the game board.

In accordance with one embodiment, the puzzle game system according to the present invention can be played solitaire (one person) or with multiple players. The puzzle game that has a scoring system and a plurality of puzzle pieces, similar to jigsaw puzzle pieces, which compete for the same puzzle location in separate but similar or identical game boards. The puzzle game includes one or more game boards having a playing area of varying shapes. The shape could be that of a human, or parts of a human or a dinosaur or a map of the United States or a musical instrument or a math symbol or a football helmet or any sort of shape, even just a square or a circle. For purposes of the description of this embodiment, the example that will be used will be that of the shape of a male human. The purpose of having the puzzle shaped like a human for this example will be to devise a puzzle game based on health and wellness; however a wide variety of game themes could be used such as sports, geography, horse breeding and health and many more. In this example of a male human, each puzzle piece will have an image and/or words on the front side of the puzzle pieces that depict certain elements that contribute to the health, or unhealthiness, of the person. Such elements could be edible items or different types of physical activity or the like.

In a first embodiment the puzzle apparatus consists of puzzle pieces formed in certain shapes to accommodate the overall shape of the puzzle playing area, similar to, but not limited to that of a jigsaw puzzle shaped as a male human. The puzzle pieces can be made of many various materials such as standard paper puzzle pieces or card board or wood or plastic or metal or a variety of other materials but in the case of this example, the materials will be of a flexible, rubber-like magnetic material. Although many other materials can be used such as paper, cardboard, plastic, ridged magnets and many other materials, the puzzle pieces must not fall out when the puzzle is turned over from its front side to its back side. Velcro, magnets or a tight fit or enclosing the puzzle pieces within a page in a book to hold them in place or placing a cover over the puzzle pieces or another attachment type of any means should be used to hold in the puzzle pieces when the puzzle board is turned over. An image is presented on the front of each puzzle piece. In this case, the images will vary from piece to piece, and the images will represent certain types of edible items and different types of physical exercises. For example, the edible items may be food and drinks, but are not limited to food and drinks. The edible items may include vitamins, drugs, herbs or any type of item that can enter the body by ingesting, injecting or any other means. For example, a male human game board, the puzzle pieces may be images of common food and drinks typical of what you would find on a restaurant menu. For this example, in addition to edible items, some of the puzzle pieces may also display images of different types of exercises. In addition to images, words may also be displayed on the front of each puzzle piece. The puzzle board may be flexible, such as made out of a combination of cloth and Velcro and made to fold up or roll up in various configurations. For purposes of this example, the configuration may be a rigid puzzle board, very similar to a typical rigid jigsaw puzzle board. In addition, the entire game can also be converted to software.

Accordingly, several advantages of one or more aspects are as follows: the puzzle may include holes or openings in the game board that allow for the scoring system to be tallied for each player simply by turning over the game board to the back side; multiple scores maybe obtained for multiple parameters from a single game play by having multiple scores for each puzzle piece and additionally allow for the game score to correlate directly to indices that offer more data of greater value to the players; and data from the indices may be related personally to each individual player using a calculation device such as a slide rule, spreadsheet, software algorithm or another similar method of deriving a calculation. Other advantages of one or more aspects will be apparent from a consideration of the drawings and the ensuing description.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein.

Corresponding reference characters indicate corresponding components throughout the several views of the drawings.

DRAWINGS

Reference Numerals

Figure 1:
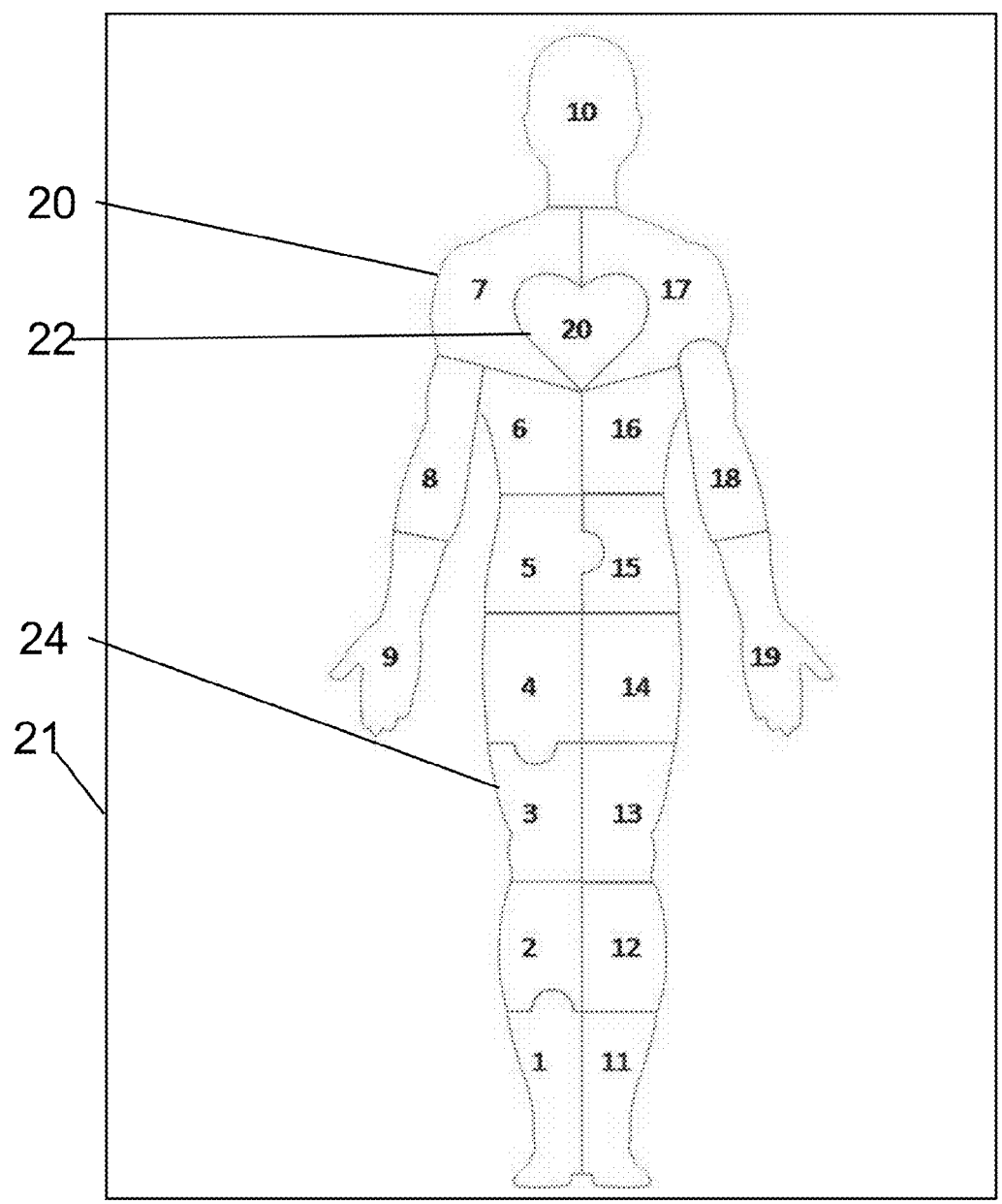
FIG. 1 is a drawing of the front of a game board of a puzzle game according to the present invention, showing 20 different puzzle locations or 20 different puzzle piece coordinates.

20 Puzzle man outline
21 Game board front side
22 Puzzle coordinate 20
24 Puzzle coordinate 3
26 Front of the game board
30 Puzzle coordinate 3 with puzzle piece installed
32 A blow up illustration of the puzzle piece that installs in coordinate 20
34 The back side of the puzzle piece that installs in coordinate 20
36 The front of the game board
38 The middle, metal section of the game board
40 The back of the game board
42 The back side of the game board
43 Legend showing hatch symbols that equal colors red, green, yellow and black
44 Puzzle coordinate 20
46 Puzzle coordinate 3
47 Hole in the puzzle board which allows the green colored dot to show through from the front of the puzzle
48 Hole in the puzzle board which allows the red colored dot to show through from the front of the puzzle
50 Score number located beside the hole in the puzzle board
52 First color on back of puzzle piece
54 Second color on back of puzzle piece
56 Third color on back of puzzle piece
58 Fourth color on back of puzzle piece
60 Material of the puzzle piece
62 Front side, graphic side of the puzzle piece
64 Back side of puzzle piece
66 Front side of puzzle piece
68 Colored dot
70 First material of puzzle piece
72 Second material of puzzle piece
74 Thickness of entire puzzle piece
76 Thickness of front side of puzzle piece
78 Thickness of back side of puzzle piece
80 Colored dot
82 Colored zone
84 Colored dot
86 Colored zone
88 Meal category
90 Description
92 Frequency in "times per month"
94 Puzzle coordinate
96 Spreadsheet section showing four different food types
98 Color designation for Cholesterol
100 Cholesterol game score for each food type
102 Actual Cholesterol value for each food type
104 Fiber content of each food type
106 Additional score points that correlate to the back of the puzzle board
108 Potassium content for each food type
110 Blood pressure game score for each food type
112 Color designation for blood pressure
114 Sodium content for each food type
116 Color designation for number of calories (weight) for each food type
118 Weight game score for each food type
120 Actual calorie content for each food type
122 Heading of "Puzzle Score"
124 Heading of "Weight Change"
126 Example puzzle game score
128 Example puzzle game score corresponding weight change
130 Front of the game board
132 Middle, metal section of game board
134 Back of game board
136 Puzzle coordinate 20 with puzzle piece installed
138 A blow up illustration of the puzzle piece that installs in coordinate 20

140 The back side of the puzzle piece that installs in coordinate 20
142 Electronic digital display for displaying the game score and/or weight change
144 Electronic digital display for displaying the game score and/or cholesterol change
146 Electronic digital display for displaying the game score and/or blood pressure change
148 Book
149 Front of the book, which is page one, which when closed, holds in the puzzle pieces
150 Page 2 of the book
152 Male human figure where puzzle pieces are to be inserted
154 Page 3 of the book
156 Page 5 of the book
158 One of the puzzle pieces that fits into the shoulder of the male human FIG.
160 Another one of the puzzle pieces that fits into the shoulder of the male human FIG.
200 Introduction
202 Main menu
204 Start new game
206 Configuration
208 Sound, animation, speed
210 Game instructions
212 High Score
214 Escape
216 Local play or on-line play
218 Escape
220 On line play
222 Login
224 On line multiplayer lobby
226 Invite friend to play
228 Friend's response
230 Two player game sequence
232 View achievements
234 Login
236 Social media
238 Share achievements
240 Local
242 One or two player
244 Choose biometric parameters
246 List of biometrics
248 One player
250 Main playing field
252 Display human puzzle outline
254 Display 80 puzzle pieces
256 Allow drag and drop of 80 puzzle pieces into human puzzle outline
258 Access pre-loaded database for each puzzle piece
260 Add score value for each biometric
262 Display the score once pieces are dropped in human puzzle man
264 Access the index database
266 Lookup score values to corresponding biometric figures
268 Display the following biometrics; weight change, cholesterol level, blood pressure
270 Save game score then game over
272 Two player game
274 Main playing field
276 Display two human puzzle-man outlines
278 Display 80 puzzle pieces
280 Require that each player take turns
288 Allow drag & drop of 80 puzzle pieces into the human puzzle-man
290 Access preloaded database for each puzzle piece in puzzle
292 Add score value for each biometric
296 Display scores as pieces are dropped into human puzzles
298 Allow both players to see each other's score
300 All pieces are in puzzle then access the index database
302 Lookup score values to corresponding biometric figures
304 Display biometrics: weight change, blood pressure, cholesterol level
306 Save game scores then game over
308 Input player's name
310 Saved high score
312 Input personal player's biometrics
314 Calculate and convert biometrics
316 Display player's biometrics, weight change, blood pressure and cholesterol level, etc.
318 Computing environment
320 Puzzle pieces

DETAILED DESCRIPTION

First Embodiment—FIGS. 1 to 12

The following description is of the best mode presently contemplated for carrying out the invention. This description is not to be taken in a limiting sense, but is made merely for the purpose of describing one or more preferred embodiments of the invention. The scope of the invention should be determined with reference to the claims.

FIG. 1 shows an example of the puzzle game. In this example, a game board 21, is approximately eleven inches high and about eight and half inches wide, however, the size of the puzzle game can vary to any size. FIG. 1 shows an example of the puzzle game including twenty different puzzle coordinates (or locations) combining to form an outline a man 20. For purposes of this example will refer to this form of a man as a "puzzle man 20". The shape of the puzzle can vary to any shape and the number of coordinates can vary to any quantity. In this example, the shape of the puzzle man 20 is a cut out in the front of the game board 21 and through the interior of the cut out is the exposed middle section of the game board 21 which is shown within the outline of puzzle man 20, which has the twenty puzzle coordinates displayed. The game board 21, can be made out of a variety of materials such as cardboard, wood, plastic, metal or any material that will allow for a puzzle shape to be placed within it or on top of it. These different materials are typically used in standard manufacturing techniques that have been in use for many years and have no proprietary or special type of manufacturing techniques required. Those skilled in the art will recognize that the game board 21 as manufactured using techniques used to manufacture known puzzles.

Location 22 shows puzzle coordinate number twenty, which is shaped as a heart. Location 24 shows puzzle coordinate number three shaped as a knee. These puzzle coordinates can be flush with the front of the puzzle board 21 or they can be recessed below the front of the puzzle board 21 or embedded within the front of the puzzle board 21.

Figure 2:
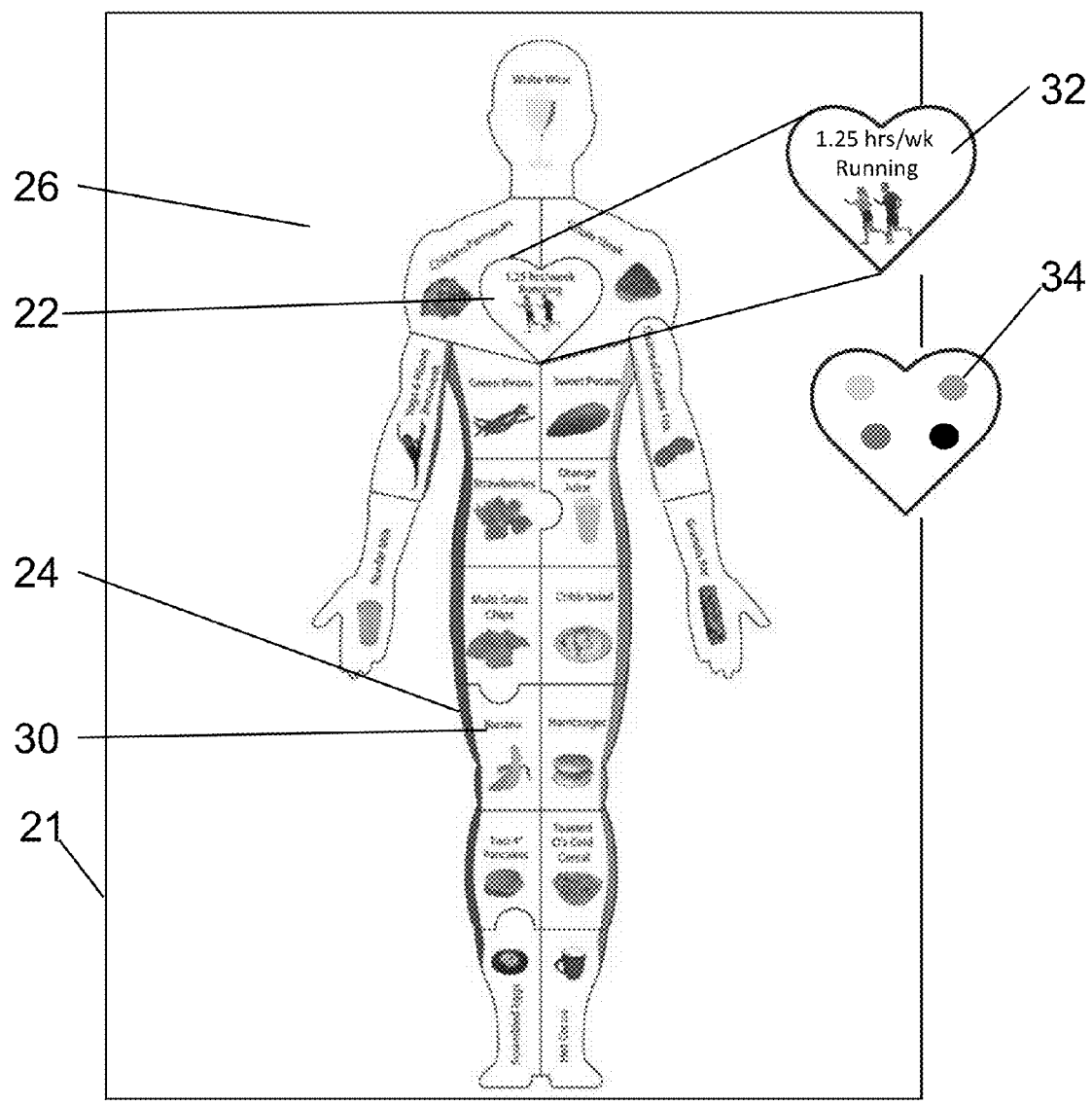
FIG. 2 is a drawing of the front of the game board with the puzzle pieces installed in the coordinates, according to the present invention.

FIG. 2 shows the front side 26 of puzzle board 21. FIG. 2 also shows puzzle piece 32 for placing inside of the coordinate 22. FIG. 2 is very similar to FIG. 1 except that FIG. 2 has had twenty puzzle pieces placed in the twenty puzzle coordinates. Coordinate 22 has puzzle piece 32 installed in it, however, 32 is a blow up of the puzzle piece shown in coordinate 22. The number of puzzle coordinates can vary from each type of puzzle design and subject matter but as shown on FIG. 1, this example of this puzzle has twenty puzzle coordinates, therefore, FIG. 2 has twenty puzzle pieces put in place. Each puzzle coordinate will have one or more puzzle pieces that will match the puzzle coordinate dimensions and one or more puzzle pieces of the same shape that can fit into the same coordinate of the same corresponding shape. This is shown in FIG. 2 for the heart shaped puzzle coordinate 22 and for the knee shaped puzzle coordinate 24. For purposes of this example, there are four alternative heart puzzle pieces 32 that will fit into puzzle coordinate 22. There are also four alternative knee puzzle pieces 30 that will fit into puzzle coordinate 24. This is also true for all of the other puzzle coordinates except they are of different shapes and with different graphics, which is further illustrated in FIG. 19. Since there are 20 puzzle coordinates and four puzzle pieces for each coordinate, then for this example, there will be a total of eighty puzzle pieces which is also further illustrated as those shown in FIG. 19. In FIG. 2, which is an example of one embodiment, all of the puzzle pieces are made out of a flexible rubber-like magnetic material that is commonly sold on the open market. In other embodiments, the puzzle pieces can be made out of any material such as paper board, plastic and a wide variety of other materials or a combination of materials. The eighty puzzle pieces are for this example only and the number of coordinates can vary and the number of puzzle pieces for each coordinate can vary and the total number of puzzle pieces can vary. The size and shape of the puzzle pieces and the coordinates can also vary. In addition, other embodiments will be described later on that offer many different materials that make up the puzzle pieces.

Each puzzle piece that will fit into a specific puzzle coordinate will be of approximately the same shape and size of the puzzle coordinate of the same shape. In the example of FIGS. 1 and 2, each puzzle piece is shaped like a section of a body part of a man such as shown by coordinates 22 and 24. On the front of each puzzle piece is the image of a type of food or drink or exercise type such as shown in 32 for the exercise of running or 30 as a banana. Heart-shaped puzzle piece 32 is shown in a larger format so that it can be more clearly seen. Typically, each puzzle coordinate will have images of foods or drinks or exercises (or other items) that compete with each other for the player's choice. In this case, puzzle piece 32 shows the exercise of running for 1.25 hours per week. The images on the puzzle pieces will vary from puzzle piece to puzzle piece, but the images are designed specifically to allow the players to make choices between consumable items and activities and compete with other players, as described in the operation portion of this embodiment. Puzzle piece 32 shows the front of the puzzle piece, however, if the puzzle piece is turned over, the back side of the puzzle piece 34 shows a mechanism or means for scoring of the game which is one of the features that makes this embodiment novel and unobvious.

In some cases where it is desired to change the front image of puzzle pieces, this can be accomplished by placing an adhesive sticker over the image such that the adhesive sticker has a new image on it. An example of this would be to change the image of a glass of straight whisky to the image of light grape juice because some adults may not want their children playing with a game piece with whisky on it.

FIG. 2, shows the back of a puzzle piece 34. Puzzle piece 34 shows four different colored dots that have been applied to the back of the puzzle piece either by paint, a sticker or silk screen or printing or other similarly known common processes. The different colors on the back of each puzzle piece of the puzzle games represent different score indicators as described in the operation section of this embodiment. The score indicators can be of any color and any shape and any quantity but for purposes of this example, four colored dots are used.

Figure 3:
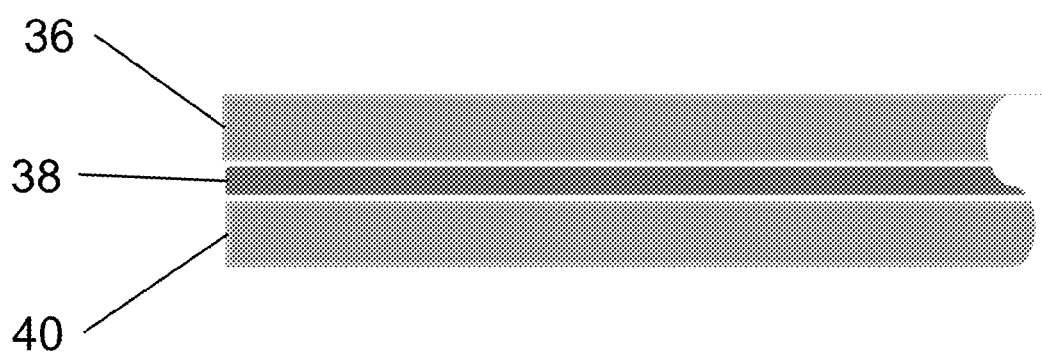
FIG. 3 is a drawing of the side view of the game board, according to the present invention.

FIG. 3 shows the side view of the game board showing the front of the puzzle board 36, the middle 38 and the back 40. For the example of this embodiment, the middle 38 is made of a metal material that allows magnetic puzzle pieces to stick to it, however, it could be made of a material that allows Velcro to stick to it or any other means of having the puzzle pieces attach to the puzzle such that they will not fall out if the puzzle is turned over on its back side. The materials of the front 36 and the back 40 can vary from foam to plastic to cardboard to wood to stone or glass or any other material desired. Boards 36, 38 and 40 can be manufactured separately and then attached or sandwiched together by using adhesive or any other common joining material or method such as laser welding or any other common technique.

Figure 4:
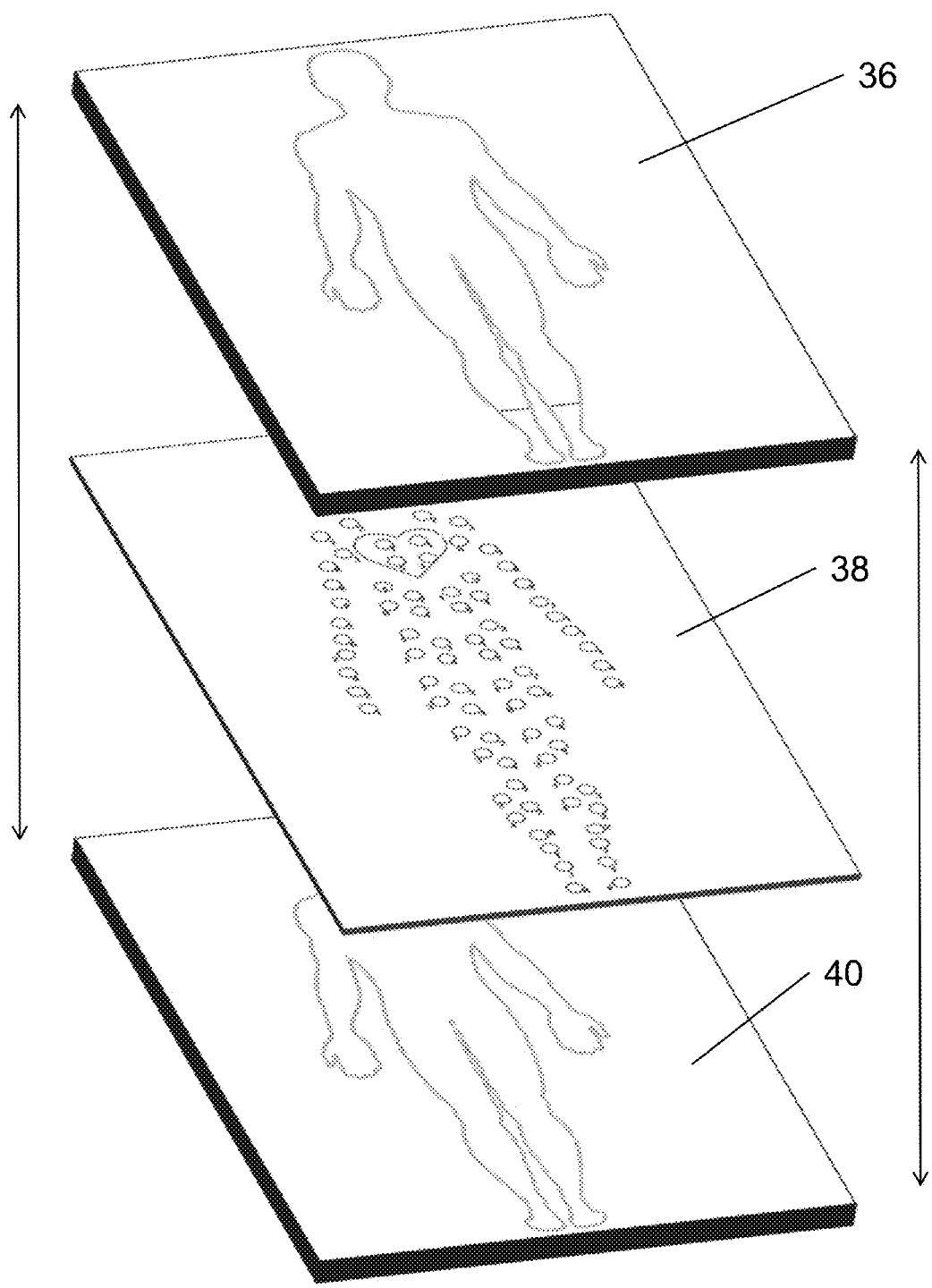
FIG. 4 is an exploded view of the puzzle game showing the front (or top) section of the game board, the middle section, and the bottom section, according to the present invention.

FIG. 4 shows the front 36, the middle 38 and the back 40 of the game board. Again, 36, 38 and 40 are sandwiched together to form the simplest form of this example of a puzzle game. It should be noted that there can be more than three layers depending on the aesthetic appeal and also if a scoring sheet of paper or plastic is required or if additional paper layers are needed to show the outline of the puzzle.

Figure 5:
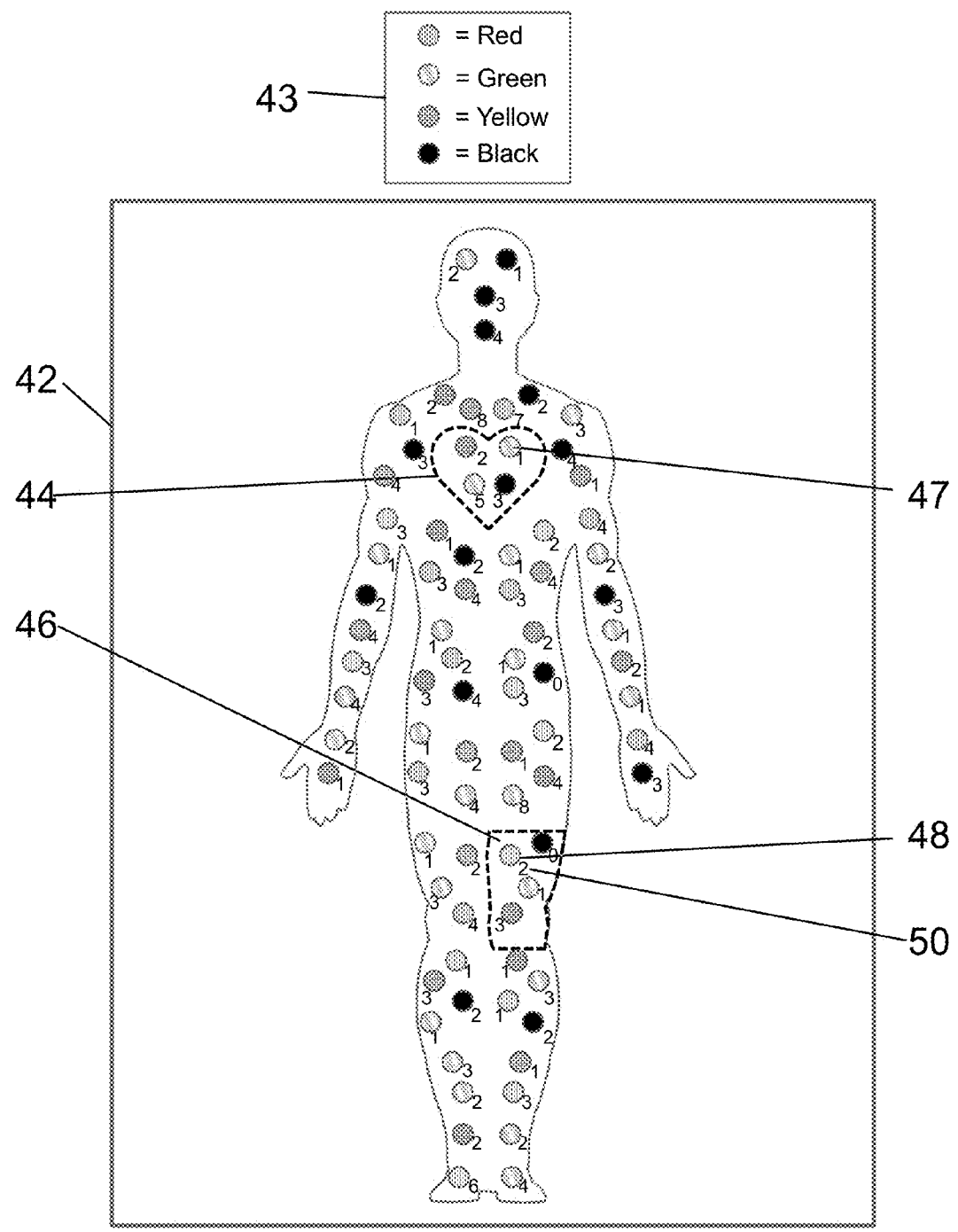
FIG. 5 shows the back of the game board showing the locations of holes and scores, according to the present invention.

FIG. 5 shows the back side of the game board as 42. In accordance to PTO 37 CFR 1.84(n), a legend is included in FIG. 5 to show the symbols that designate different colors that are used in FIG. 5. The color symbols in legend are shown as legend 43 in FIG. 5. Heart-shaped puzzle coordinate twenty is shown as area 44. Although area 44 is shown on the back of the puzzle board, it is the same puzzle piece coordinate location as FIG. 1 coordinate area 22 and FIG. 2 coordinate area 22. Area 44 has four holes in it with one of the holes being shown as hole 47. Knee shaped puzzle coordinate three is again shown as area 46. Although area 46 is shown on the back of the puzzle board, it is the same coordinate location the puzzle piece coordinate area 24 shown in FIG. 1 and also in FIG. 2 coordinate area 24. Since FIG. 5 is the back of the puzzle board, the puzzle piece coordinates are basically located as a mirror image in comparison to the front side of the puzzle board, such as the front sides shown in FIGS. 1 and 2. Within puzzle coordinate 46, there are four holes with one hole being shown as hole 48. These holes were punched through the puzzle board using a very simple metal punching tool, however a drill or stamping machine or die mold or any similar hole penetration tool or method can be used. Shown beside hole 48 is score 50 which shows a score of "2". All of the holes shown in FIG. 5 have scores beside each hole. In this example, there are a total of 82 holes and 82 scores. In this example, the scores are all single digit numerals to make the score adding or tallying very easy for each player however, the scores can be of any organized set of numbers or figures including, but not limited to double digit, triple digit or the like. The scores can be applied directly to the metal or painted on or printed on any material by any common means. Holes 47 and 48 are shown to have colors on backs of the puzzle pieces being displayed through holes 47 and 48. In this case, the back of a puzzle piece inserted in area 44 shows a color green through hole 47 and back of another puzzle piece installed in area 46 shows a color red through hole 48. The purpose of the different colors is so that the players can add up or tally up the scores that correspond to a specific color. In this case the player would add up their scores for all of the green dots that show through the holes. Then the player would add up all of the scores beside the red dots that show through the holes. Then the player would add up all of the scores beside the yellow dots that show through the holes. They would then have a respective total score based on green, another score based on red and another score based on yellow. All embodiments are not limited to the use of only green, red and yellow, and any set of colors can be used and any number of different colors can be used. The back of the puzzle board can also act as a storage space for the puzzle pieces when the game is not in use. In this example, there are two puzzle boards and four sets of puzzle pieces, therefore all puzzle pieces can be stored in the game my placing the puzzle pieces in their proper puzzle coordinate locations on the front side of each puzzle board and also on the back side of each puzzle board. This method of storing the puzzle pieces when the game is not being played is also a method of making sure all of the pieces are not lost. If all puzzle coordinates on the two front sides and the two back sides of the puzzle boards are full, then all of the pieces are present and none are missing or lost. Many other storage means for the puzzle pieces can be used such as a plastic bag or a small box or the like.

Figure 17:
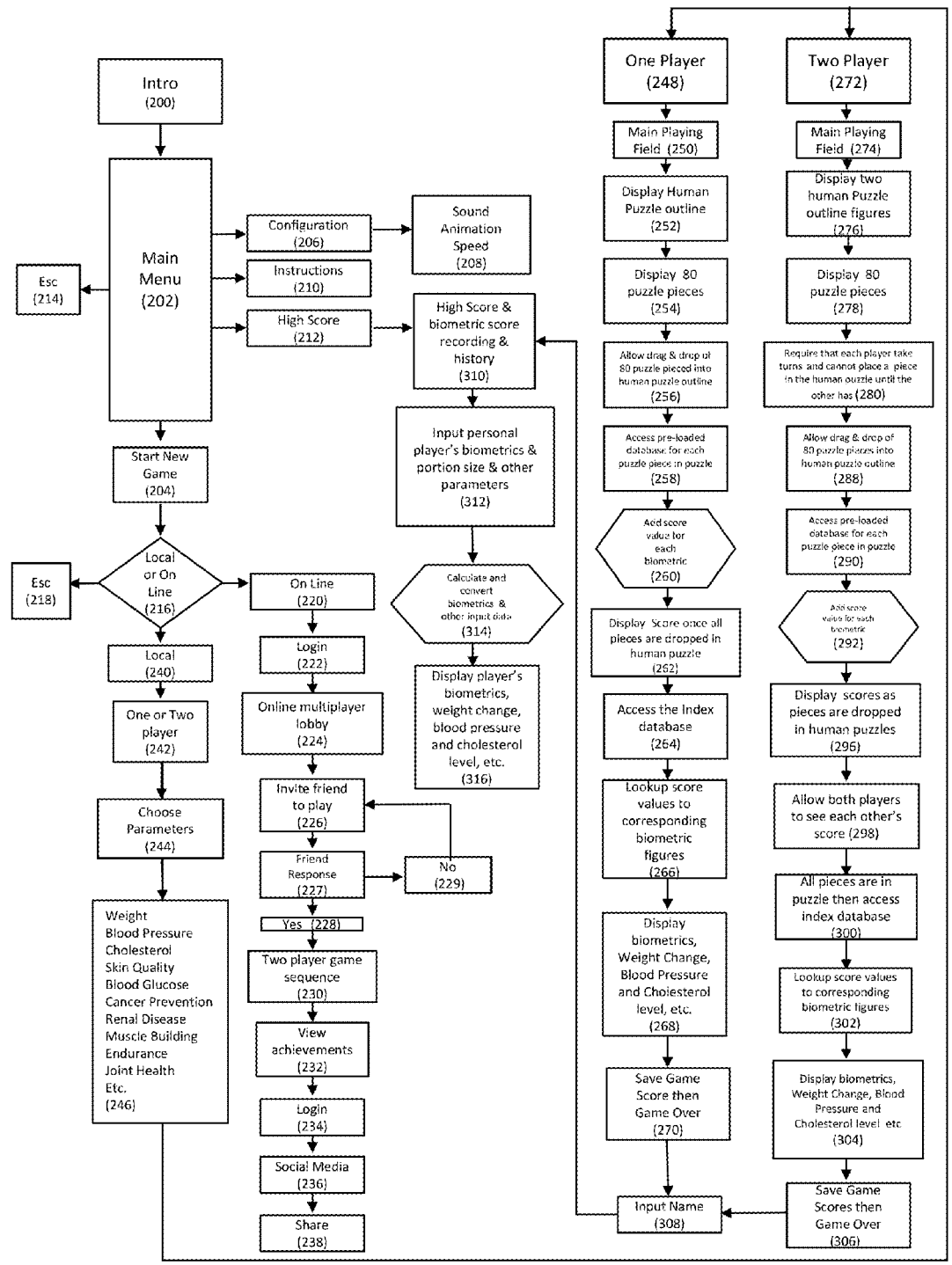
FIG. 17 shows steps of a software embodiment of the puzzle game, according to the present invention.

Another feature of FIG. 5 involves using a smart phone "App" or application, to take a photo of a completed puzzle score board, such as that shown in FIG. 5. A smart phone app could automatically add up all of the player's scores. There are many known smart phone applications "Apps" that can perform optical character recognition (OCR). OCR exists on nearly all available smart phones. In addition, color recognition software is readily available and even free to download from the Internet. OCR recognition software and color recognition software are common software technologies that are readily available and can be easily modified to accommodate this embodiment. In addition, the OCR and color recognition software could be combined with the software flowchart shown in FIG. 17, blocks 258, 260, 262, 264, 266 and 268. FIG. 17 will be described below under the "FIG. 17" section of this description section. The combination of these two software technologies would enable game players to quickly add up their scores for said game and said human puzzle man. The App would also allow for a means to quickly see corresponding biometric parameters such as those shown in FIG. 11, which is later described under the "FIG. 11" description. Biometric parameters could include such categories as weight change, blood cholesterol level change, blood pressure change, blood glucose level change, skin quality change, antioxidant consumption level (cancer prevention), protein consumption (renal disease) and several other biometrics and parameters.

Figure 6:
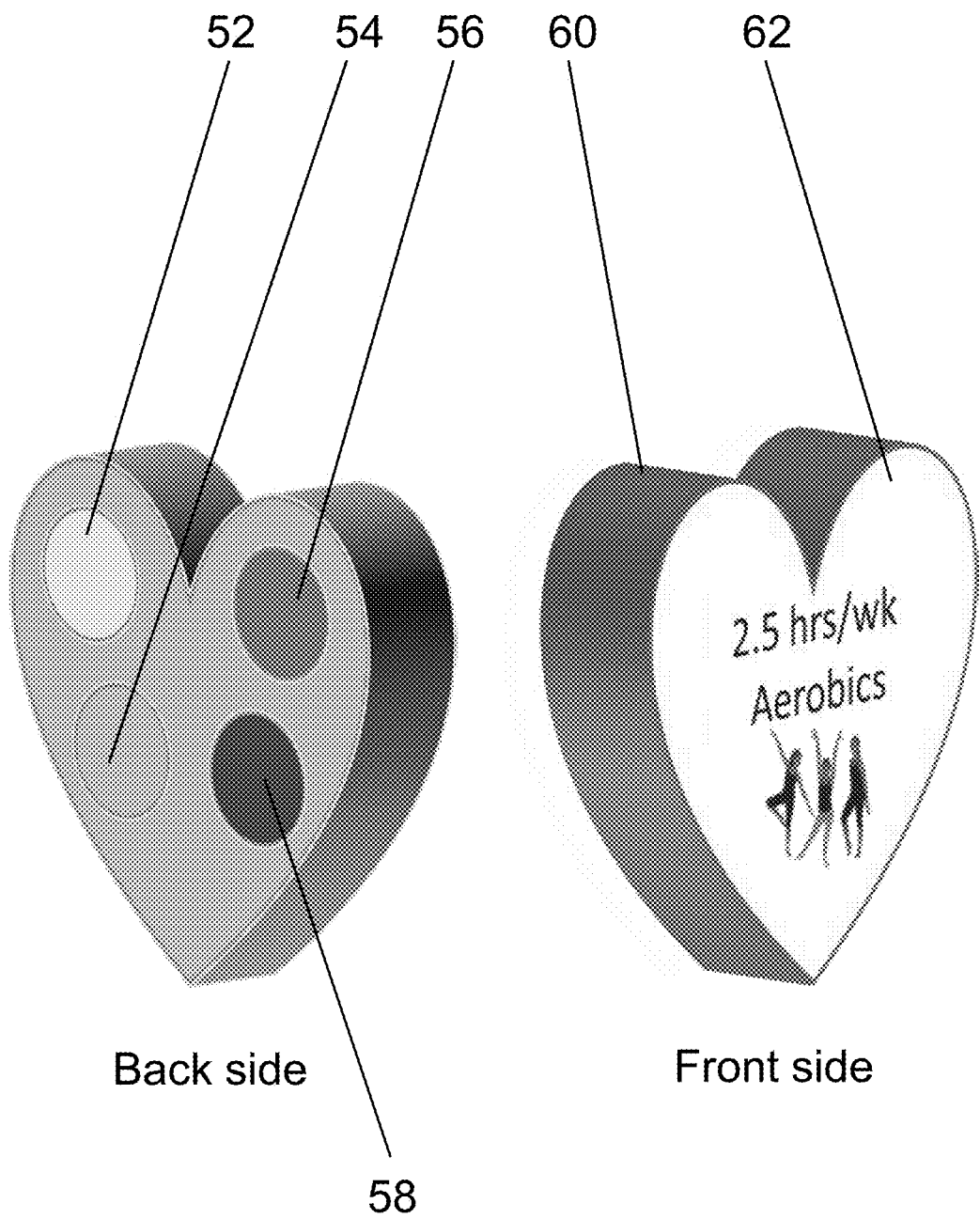
FIG. 6 shows a detailed view of one puzzle piece constructed out of a single material, according to the present invention.
Figure 10:
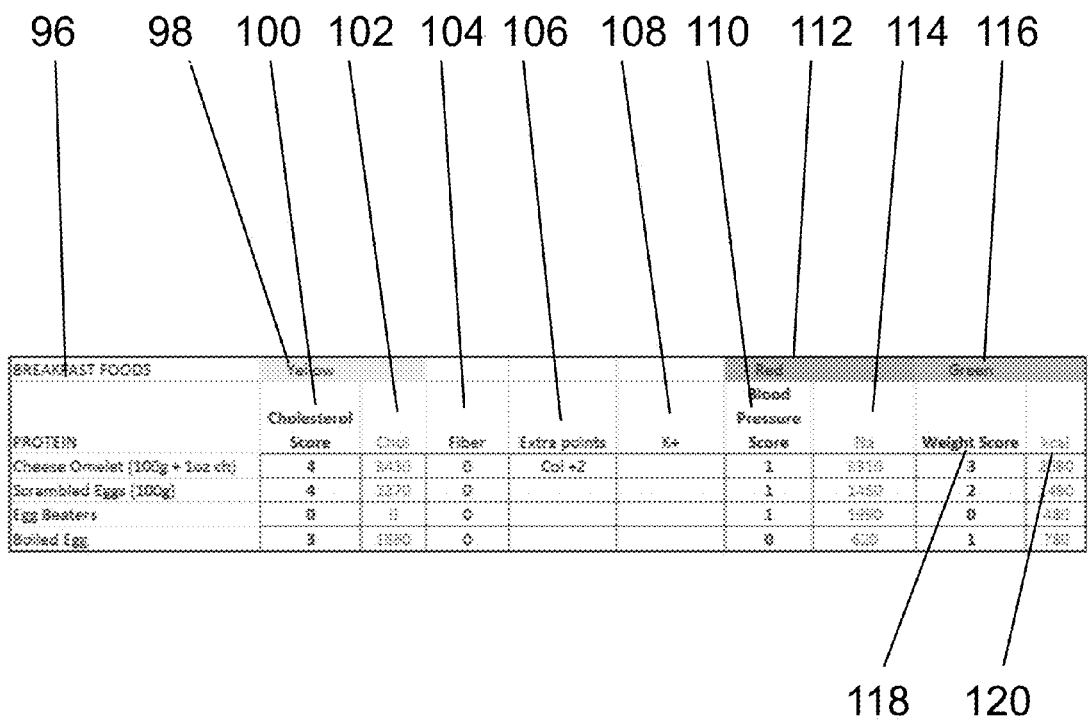
FIG. 10 is the a portion of a matrix that is used to determine what score for each of three biometrics (weight, cholesterol, blood pressure) is to be applied to each puzzle piece, according to the present invention.

FIG. 6 shows an enlarged view of a single puzzle piece. In this case, the heart-shaped puzzle piece from coordinate 20 of the male human puzzle example is shown, however, this could be any puzzle piece from an embodiment of this game. FIG. 6 shows that there are indicia 52, 54, 56 and 58 on the back side of the puzzle piece in the form of colored dots. The indicia 52, 54, 56 and 58 can be any recognizable patterns, designs, or colors but in the case of this example, yellow, red, green and black are used to make up the four colors on the back side of a puzzle piece. Yellow correlates to the designation for cholesterol as shown in FIG. 10, column 100. Red correlates to the designation for blood pressure as shown in FIG. 10, column 110. Green correlates to the designation for weight as shown in FIG. 10, column 116. Black does not correlate to anything. Black is purposely left to count as "no score" toward the game score. Again, any colors can be used for an embodiment as long as the colors properly correlate to a parameter or a biometric in the game or to a "no score" condition. Although dots 52, 54, 56 and 58 are in the form of circular dots used as score designators, the shape of these score designators do not have to limited to circular dots. The score designators can be of any size, any shape and any color. In addition, these dots could actually be letters or numbers or symbols, they are not limited only to different geometric shapes. Figure six shows the side of the puzzle piece as 60 which is designating the material of the puzzle piece. In this case, the major portion of the puzzle piece is made out of one material. The material can be paper board, plastic, wood, rubber, glass, ceramic or marble or any other material depending on the embodiment chosen, however, in the case of this example for the first embodiment, flexible magnet material is chosen to be the primary material of this puzzle piece. Dots shown as indicia 52, 54, 56 and 58 can be printed on the back of the puzzle piece or they can be glued on or applied by any other common means of printing or attaching colors to the surface of an object. Puzzle surface area 62 shows the front side of the puzzle piece, which is the graphic side of the puzzle piece. The graphic shown on surface 62 could be printed directly on the puzzle piece, or it could be printed on a different material such as paper, laminate, plastic or any other material that can be printed on and then adhered to the puzzle piece. Although FIG. 6 does allow for the puzzle piece to be composed of several different materials, which includes colored ink, laminate paper plus other materials, but the bulk of the material that makes up the puzzle piece 60 is primarily one material.

Figure 7:
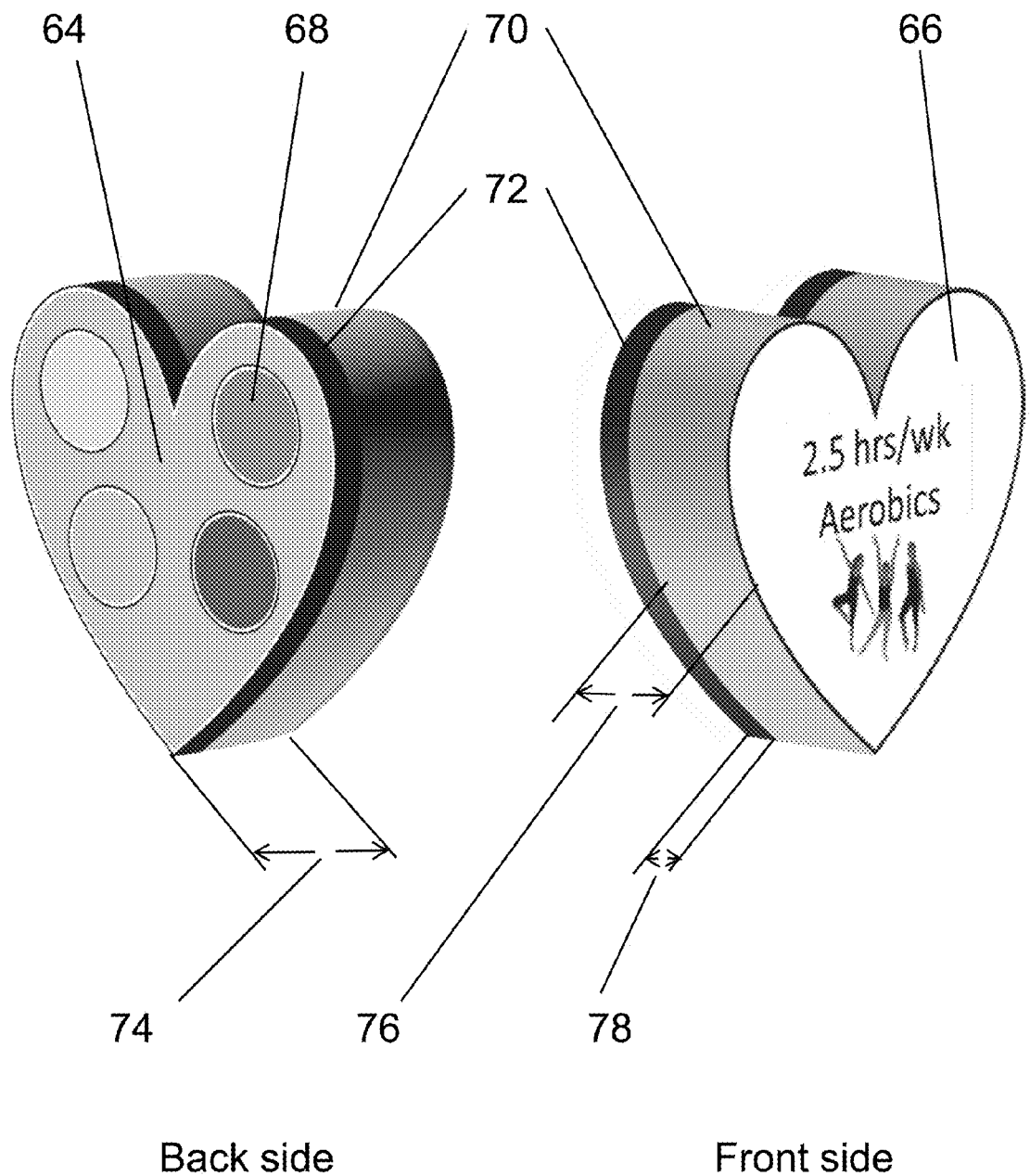
FIG. 7 shows a detailed view of one puzzle piece constructed out of more than a single material, according to the present invention.

FIG. 7 shows a detailed view of a single puzzle piece similar to the puzzle piece in FIG. 6, however, the puzzle piece in FIG. 7 is composed on multiple materials. The back side 64 of the puzzle piece and the front side 66 of the puzzle piece are shown. The back side 68 is showing a colored dot exactly as described for 56 in FIG. 6. An edge view 70 shows that the puzzle piece material toward the front of the puzzle piece is composed of one material while edge view 72 shows that there is another, different material shown toward the back of the puzzle piece. These various materials sections of the puzzle pieces can be composed of a variety of different materials or different components. The different sections of the puzzle pieces can even contain electronic components which will be explained further in the third embodiment described later in this description section. For purposes of this first embodiment, the material designated as edge view 70 shall be of a standard paper board or card board material with a thickness designated as 76 which can be any thickness, but for this example we will use 2 millimeters. Edge view 72 will be composed of a flexible magnetic with a thickness shown as 78, which can be any thickness but for this example, we will use 1 millimeter. Edge views 70 and 72 can show any materials, such as wood, plastic, magnetic material or paper board or a variety of other materials. In addition, there can be more than just two materials; there can be plurality of different materials with a plurality of layers. The materials should be of a combination that makes the puzzle piece functional so that it will fit into the puzzle board assembly and also remain in the puzzle assembly when the puzzle board is turned over to the reverse side. Dimension 74 shows the overall thickness of this particular puzzle piece which could be of any thickness but for purposes of this example, the thickness can be 3 millimeters. Edge views 70 and 72 show material adhered together by any common means and the manufacturing process is such that the materials can be adhered before or after die cutting. The purpose of using multiple materials is for functional, aesthetic and cost purposes but not limited to these purposes. In this example, adhering a lower thickness magnetic material (flexible or inflexible) to paper board will result in a lower cost puzzle piece compared to the entire puzzle piece composed primarily of magnetic material as described in FIG. 6. Adding in a back layer of magnetic material onto the paper board puzzle piece will enable the function of attaching the puzzle piece to the puzzle board. Combining together the paper board and the magnetic material will be a much lower cost as compared to the entire puzzle piece being primarily magnetic material.

Figure 8:
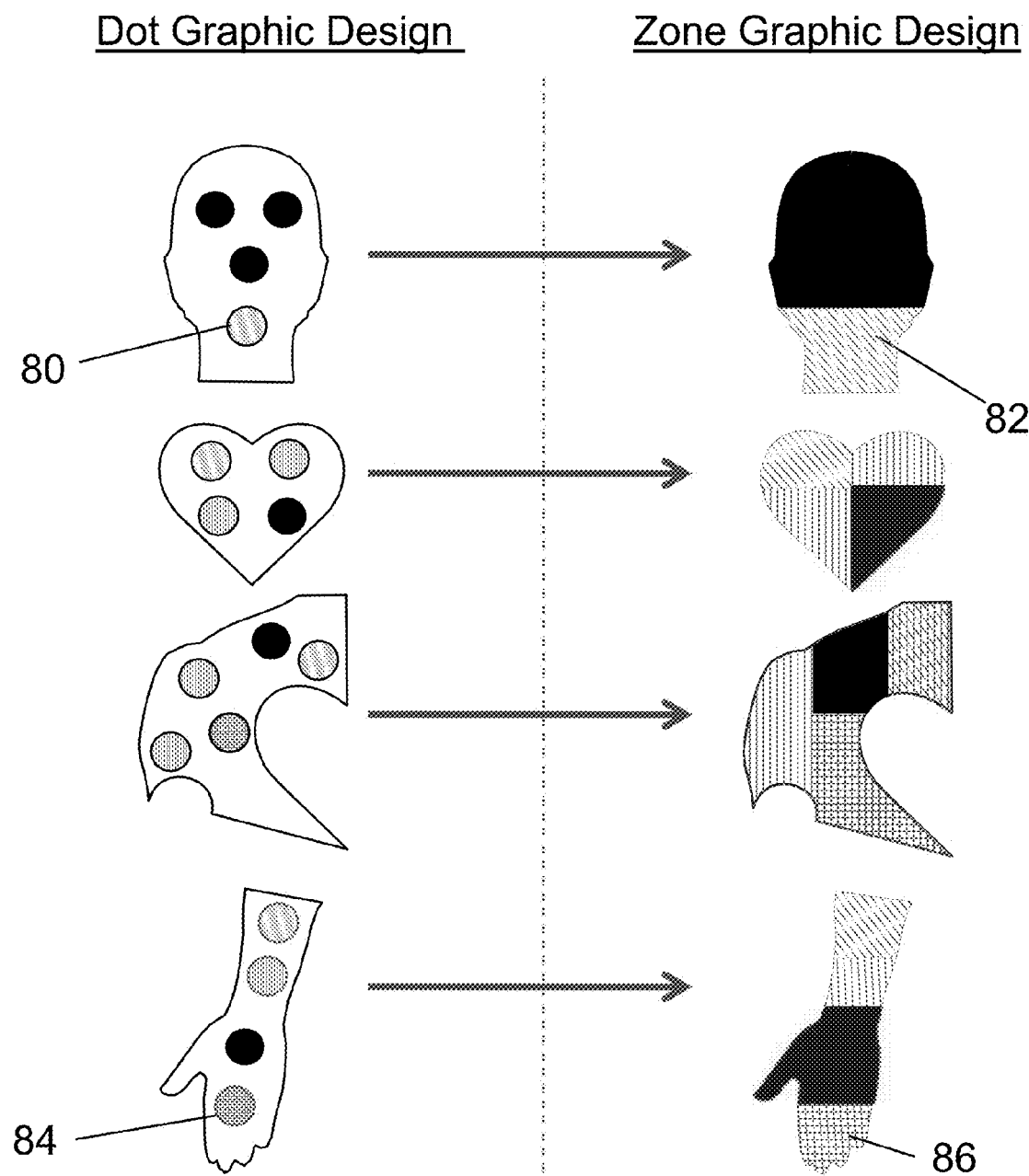
FIG. 8 shows two different graphic designs for the back of four puzzle pieces, according to the present invention.

FIG. 8 includes symbols for colors exactly as shown in legend 43 in FIG. 5. Colors shown in legend 43 are examples of colors only, any color or combination of colors can be used in all embodiments. FIG. 8 shows the back side of puzzle pieces, but in this case, four puzzle pieces are shown. All color symbols shown in legend 43 also apply to FIG. 8. Indicia is shown as a colored dot 80 in a dot graphic design and as a colored zone 82 in a zone graphic design. A colored zone offers the same function as the colored dot, however, a colored zone offers a much larger area of colored area which is a benefit to manufacturing. Colored dot 84 also shows a colored dot and the corresponding colored zone would be 86. The use of dots versus the use of zones is an example of previously stating that the colored dots can be of any size or shape or indicia, even including, but not limited to numbers, symbols and letters. In this example, the colored zones offer a substantial benefit to the manufacturing process due to the registration that is required between the colors on the back side of the puzzle pieces, (such as 80 or 82 or 84 or 86) and the holes in the back side of the puzzle board shown in FIG. 5.

Figure 9:
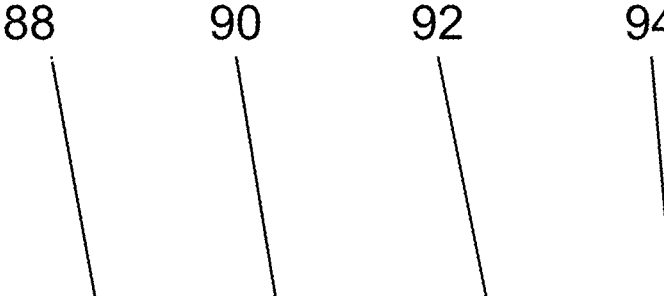
FIG. 9 is a frequency table, according to the present invention.

FIG. 9 shows one of the elements used to calculate the scoring system for this embodiment. A large amount of data must be collected for this example of this embodiment. In this example, data was collected for three biometric parameters stemming from calories, sodium and cholesterol. In order to calculate the scoring system, one component of the calculation that should be included is the frequency in which calories, sodium and cholesterol are ether consumed by the puzzle man, or burned off by the puzzle man via exercises. Another component of the calculation that is needed to set the scoring system is the standardized, fixed physical characteristics of the puzzle man. In this example, the physical puzzle man is shown in FIGS. 1, 2, 4, 5, 14, 15 and 16. The fixed physical characteristics of this example is a man that weighs 195 pounds. He also sits at his desk at work 50% of the time. He also consumes about 2800 calories, 4400 milligrams of sodium and 379 milligrams of cholesterol each day. The calculation for the scoring system is performed using the established physical characteristics of the puzzle man in combination with the frequencies of consuming items and performing the exercises in FIG. 9 over a 30 day period of time. FIG. 9 shows the frequency of all 80 puzzle pieces that are designated for the 20 puzzle coordinates in the example for this embodiment. Column 88 shows the meal category of the types of foods, such as dinner, lunch and breakfast. Column 90 shows the description of all items be it a food type or a type of exercise. Column 92 shows the frequency in regard to how many times per month the puzzle man will be consuming the foods or drinks or performing the exercises. Column 94 shows the puzzle coordinate for all 20 coordinates of the puzzle man. Once again, this embodiment is not limited to the number of coordinates, or the number of puzzle pieces or the number of meal categories or the number of food types or exercise types, or frequencies or the duration of the period of time that the frequencies occur. FIG. 9 shows a table based on a duration period of 30 days. This duration could be adjusted to any period of time, such as days or months or years. All of these factors are highly flexible, however, for this embodiment example, these factors are needed in order to calculate out the scoring system thereby enabling the game to provide one or more scores for the players. A novel feature of this game is that the player or players have the ability to make a choice to use only one score or a plurality of scores to determine the winner of the game.

FIG. 10 shows a section of a spreadsheet that illustrates how the scoring system was determined for one sample puzzle coordinate using the information from the puzzle man's physical characteristics in combination with the frequency table in FIG. 9. In FIG. 10, column 98 shows that there are four different types of foods matching four different puzzle pieces that will fit into puzzle coordinate number 1, in this case the four food types are cheese omelet, scrambled eggs, egg whites and a boiled egg. Spreadsheet cell 98 shows that the color to be used to designate cholesterol will be yellow and column 112 shows that red will be for blood pressure and column 116 shows that green is the color to designate weight. The different colors are the colors that will be used on the back of puzzle pieces such as those as shown in FIG. 2, colored dot 34, and also shown in FIG. 6, dot 58, FIG. 7, dot 68 and FIG. 8 dots 80 and 84. Scores 100 represent Cholesterol scores. Scores 110 represent blood pressure scores. Scores 118 represent weight scores. Scores 106 shows an extra score column used when another, fourth score hole is needed for a particular score balance within a coordinate. In this example the score in column 100 shows that the cheese omelet has a cholesterol score of four score points. In column 110 the cheese omelet has a blood pressure score of one score point and in column 118 the cheese omelet has a weight score of three score points. The scores are calculated and based on the levels of cholesterol shown in column 102 and the level of sodium shown in column 108 and the number of calories shown in column 120. The higher the cholesterol content or the sodium content or the higher the calorie content, then the higher the score will be for each biometric relative to the other types of foods within the same puzzle coordinate. The scoring system is designed to make the scoring very easy for the player. The calculation for the scoring system requires a balancing among and between, the three different biometrics (weight, blood pressure and cholesterol level) resulting from a calculation means such that the scores must be derived among the four colors, or four score indicia, on the back of each puzzle piece which correspondingly show through the four holes on the back of the puzzle game board. This scoring system is one of the most unobvious and novel features of the embodiments. There has never been a scoring system like this for a board game using jigsaw puzzle pieces whereby the players have the choice of using one or more scores, or a combination of more than one score, to determine the game winner.

Figure 11:
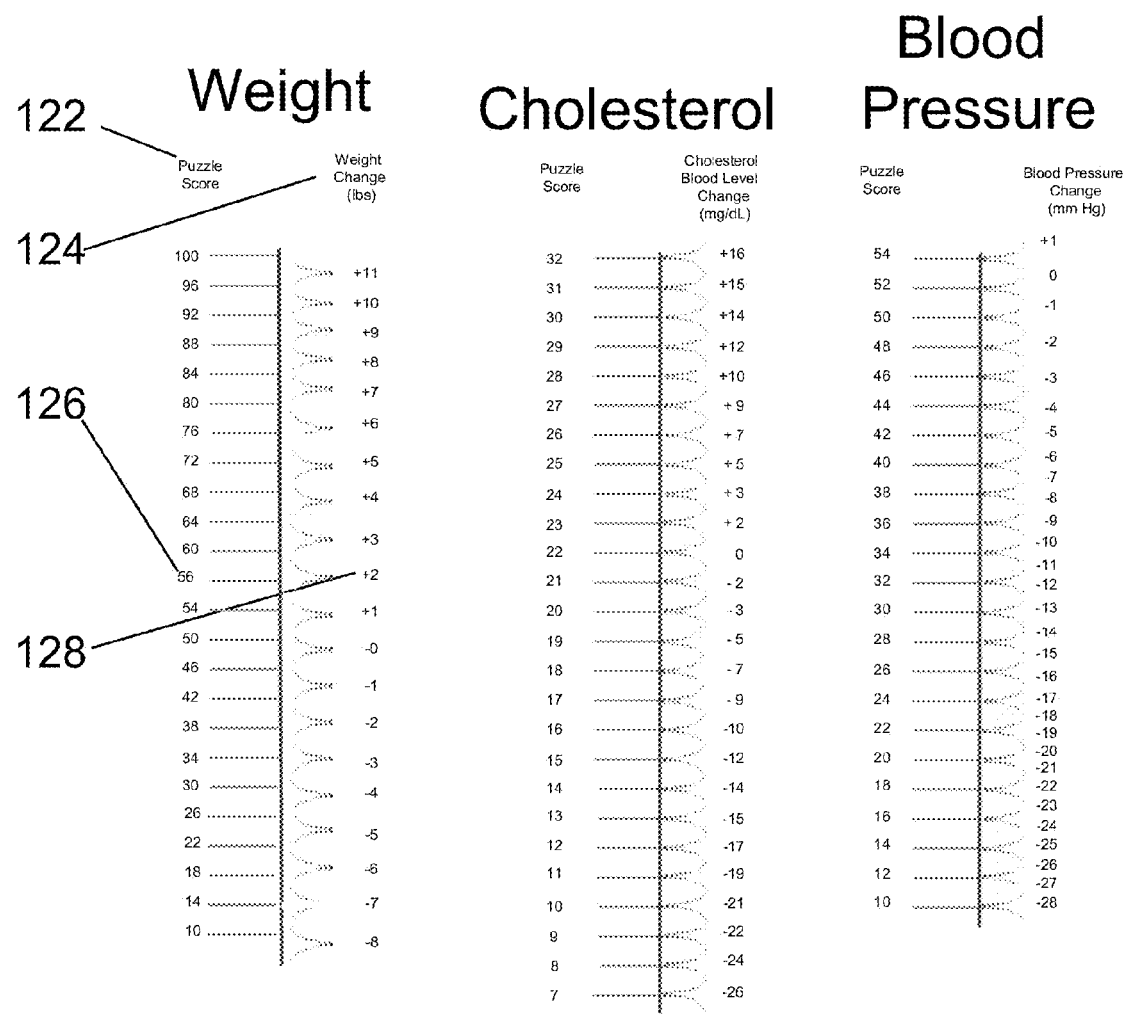
FIG. 11 is an illustration of the Indices that correlate the game scores to Weight, Cholesterol and Blood Pressure, according to the present invention.

FIG. 11 shows an example of an index that will accompany the puzzle game. In this example, an index is shown with a puzzle score column shown as 122. Column 122 corresponds to a weight change column 124. In this example, calories are used to calculate the score for each type of food that is designated and printed on the front of each puzzle piece. An example would be the number of calories for the banana on the puzzle piece 30 in FIG. 2. The number of calories relates to a scoring system on the back of the puzzle board as shown in FIG. 5. The calorie level for all foods, drinks and exercises that are included in this example of this embodiment are sourced from numerous Government and other publicly available references. The index shown on FIG. 11 for weight as well as cholesterol and blood pressure are based on all of the food, drinks and exercises for the puzzle pieces in this example, some of which are shown on FIG. 2. Score 126 shows a sample score of 56 for a player in the weight biometric which then corresponds to biometric 128 which shows that the score of 56 caused the human puzzle man to gain two pounds of body weight. A copy of the index should accompany the puzzle game in order for a player to determine the effect their score has on the weight, cholesterol and blood pressure of the puzzle man in this example.

Figure 12:
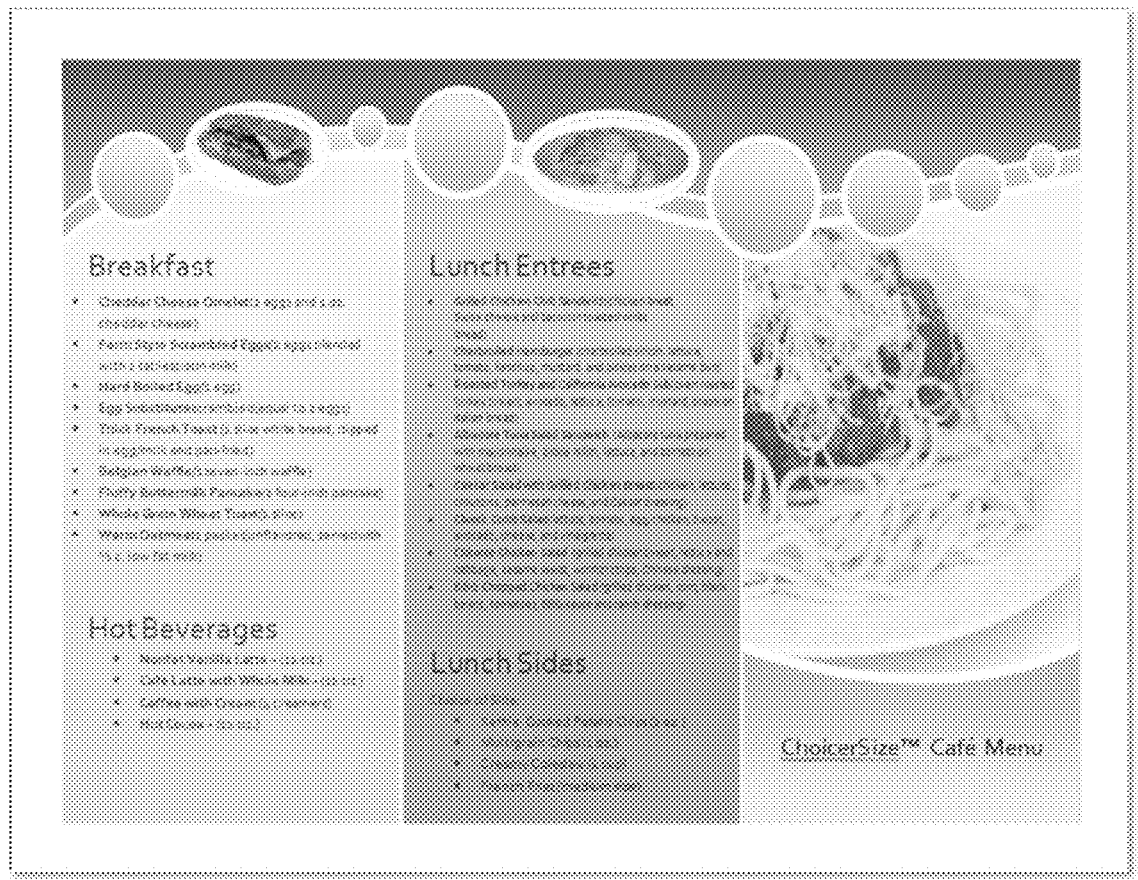
FIG. 12 is a menu that shows portion sizes of the foods on the puzzle pieces, according to the present invention.

FIG. 12 shows a menu which could also accompany these embodiments, but it is not required for the game to function, it is an option. The menu reads like a standard restaurant menu with the added feature that portion sizes and a detailed description are a part of each item on the menu description. The menu is provided in the event that the players want to know exactly what the detailed description is for the food type and also what the portion sizes are for the food items on the front of the puzzle pieces. Portion sizes are also used in the calculation to determine the number of calories, sodium and cholesterol is contained in food items included in this example of this embodiment. Portion sizes can also be used to calculate many other biometric parameters as well as the effect that the consumption amounts have on preventing diseases or building muscle or building endurance or energy or a wide variety of biological effects on the human puzzle man in this example.

As stated previously, this example of this embodiment includes a game board having a human shape, however, the shape of the game board and of all of the embodiments in this description section can vary. Example of other shapes can be that of a dinosaur or a map of the United States or a musical instrument or a math symbol or a football helmet a horse or any sort of shape, even just a rectangle, square or a circle. Likewise, the biometrics that makes up the example of this game, such as weight, cholesterol and blood pressure, could be substituted for other parameters that make up a game with a different theme. An example would be to make the puzzle in the shape of a horse and the front side of the puzzle pieces could consist of horse food types, horse exercise types and horse breeding types in order to have output parameters such as horse speed, endurance, coat quality, strength, size, demeanor, disease resistance and other such horse related factors. In addition, another example of this embodiment using a different shaped puzzle would be to shape the puzzle in the form of a football field with the puzzle coordinates being equal to the defensive and offensive player positions. The front of the puzzle pieces would be different players from different football teams and the game players would have to decide which football players to put into their puzzle board. The output parameters in the index would be various team statistics such as average game score, total rushing yards, total passing yards and the like.

Figure 13:
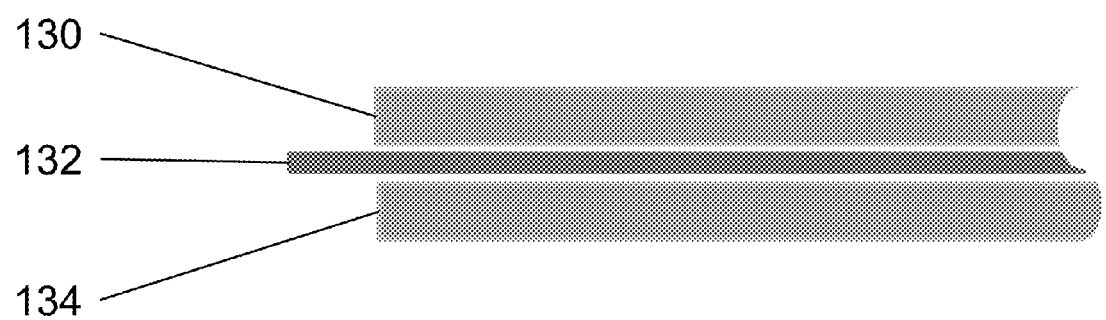
FIG. 13 is a drawing of the side view of the game board with the middle section sliding out from in between the front and back portions of the game board, according to the present invention.
Figure 14:
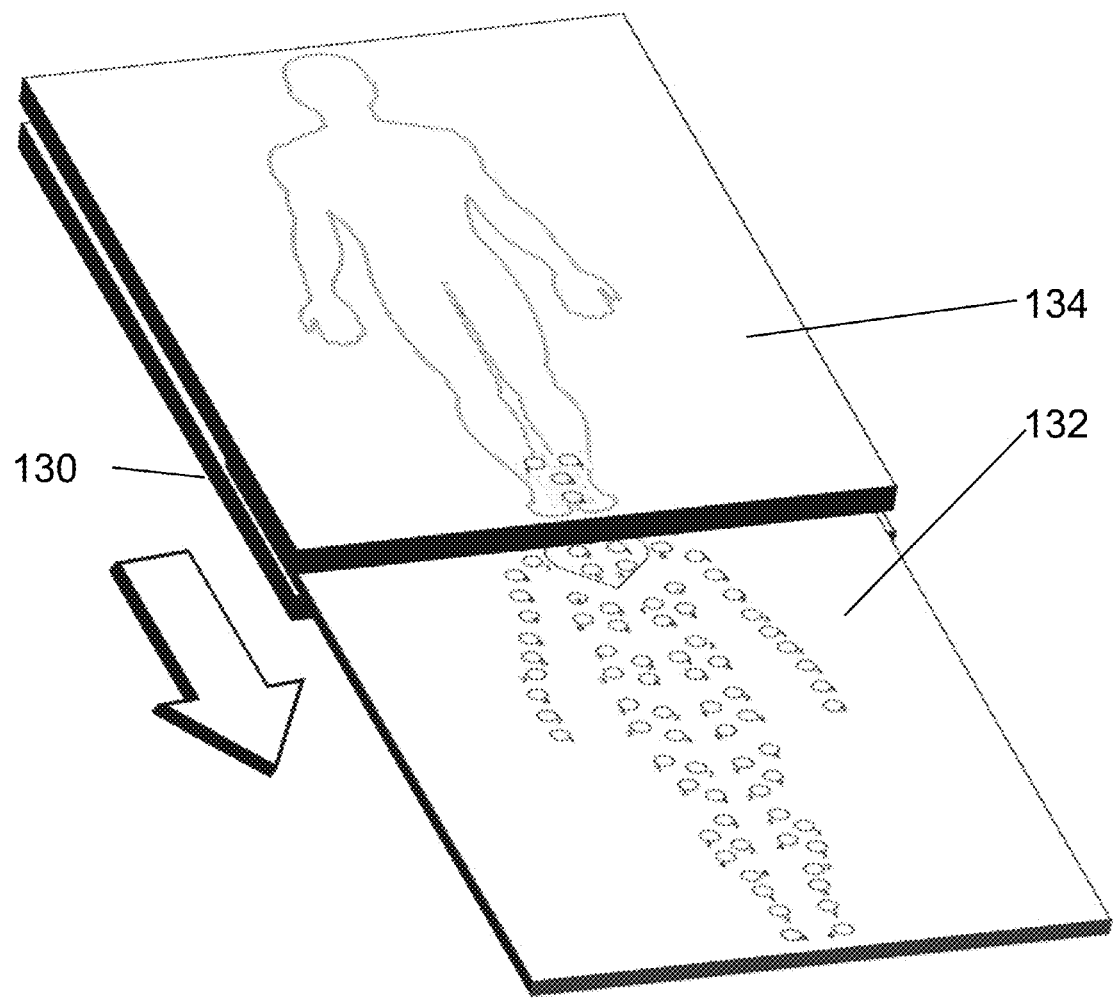
FIG. 14 is a drawing of the front of the game board showing the middle section pulling out from in between the front and back of the game board, according to the present invention.

Second Embodiment—FIGS. 13 & 14

FIG. 13 is similar to FIG. 3 but it is a slightly different design. FIG. 13 shows a side view of the game board, having a front 130, a middle 132, and a back 134. The middle 132 is a score sheet for the game board and contains the holes with scores on the back of it as shown in FIG. 5. The middle 132 is pulled out a bit or has been slid out from in between sheets 130 and 134. In this case, this design is such that 132 can be removed and then replaced with a sheet that has a different score system. An example would be to remove the middle 132 with a scoring system based on calories and replace it with another sheet that has a scoring system based on biometrics related to blood glucose level (diabetes) or renal disease or skin quality or cancer prevention or another such human health biometric.

FIG. 14 shows the top middle, and rear 130, 132 and 134 except in a different view that shows the middle section 132 sliding out from in between the front 130 and back 134 of the game board. A removable middle section 132 will enable the game to be versatile. This feature of a removable middle section 132 is an option as an alternative design to the first embodiment of the game. It is an alternative to having the middle section 132 permanently adhered to the front of the game board 130 and the back of the game board 134. The sliding mechanism can be designed in many ways including a simple pressure release system or a Velcro system or a latching system or any other common means of sliding out a thin sheet of material out from in between other sheets.

Figure 15:
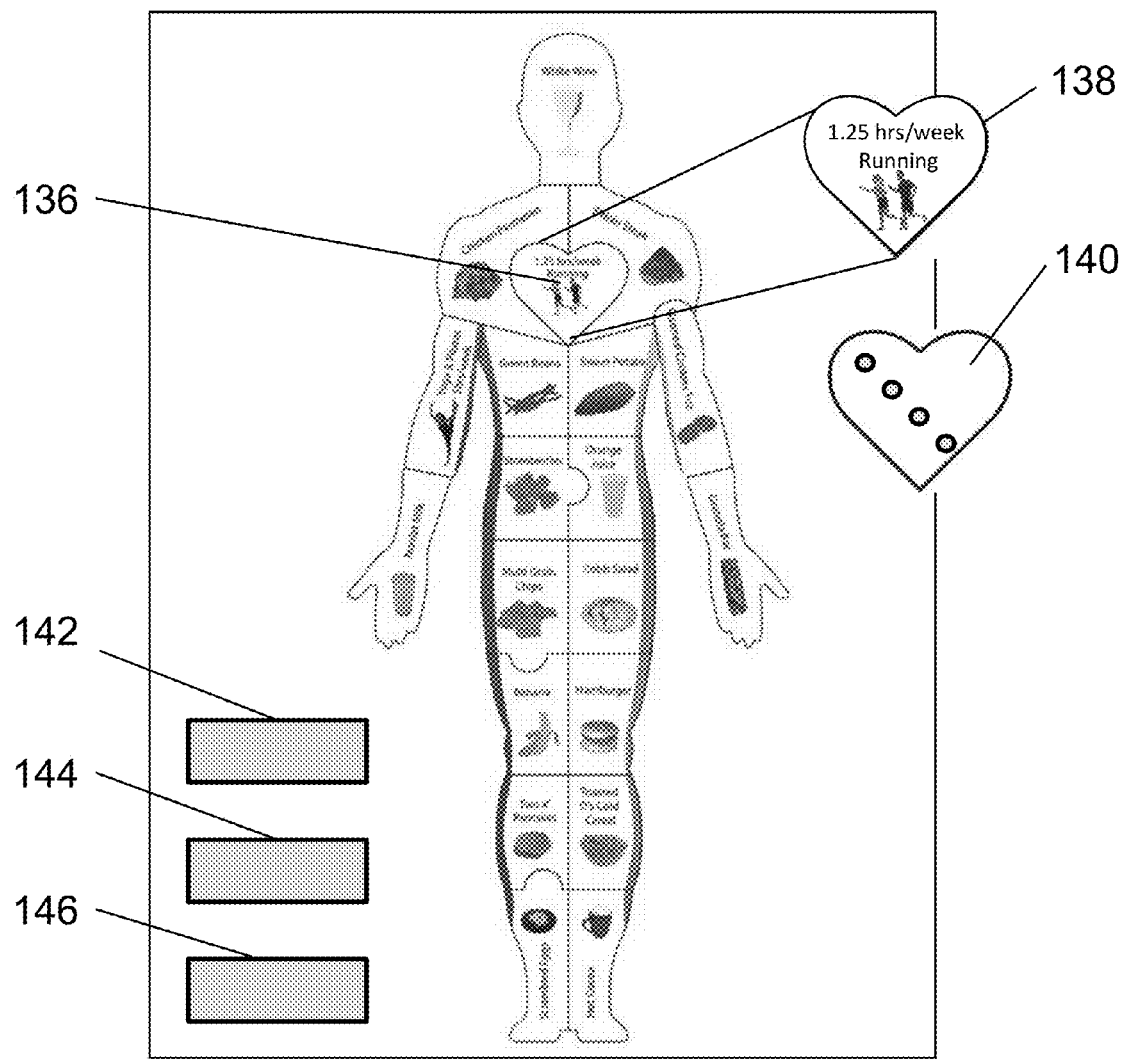
FIG. 15 is a drawing of the front of the game board but this is the electronic version with three electronic digital displays, according to the present invention.

Third Embodiment—FIG. 15

FIG. 15 shows the same basic description of the first embodiment except FIG. 15 is based on a version using an electronic scoring system. For proper viewing pieces, puzzle piece 136 is enlarged to become puzzle piece 138. The back of puzzle piece 138 is back side 140. Puzzle piece 138 shows that it is based on 1.25 hours per week of running. The piece 140 includes four electronic switch triggers which could be colored dots or color emitters or signal emitters or magnetic sensors or magnetic switches or any other type of existing or common technology for transmitting a signal or an indicator from one location to another. In this example, colored dots are used on the puzzle piece and an electronic color detector is used on the electronic puzzle board.

The summing of the scores is then done electronically by a small microprocessor embedded in the puzzle board and electronic or digital displays 142, 144 and 146 are used to display the three different scores that can be obtained by playing the game. The number of electronic displays for this embodiment is not limited to only three, there can be just one electronic display or a plurality of electronic displays. The size or shape of the electronic displays can also vary. In addition, the electronic displays are not limited to being positioned as shown in FIG. 15, they can be in any position on the game board or they can be remotely connected via a wire or even a wireless system. In this embodiment, there are no holes on the back of the game board, instead there are just electronic emitters and electronic receivers on the back side of the puzzle pieces and the inside back of the puzzle boards where the back of the puzzle pieces are placed.

The electronic or digital displays 142, 144 and 146 can have a means to display the scores real-time as the player inserts the puzzle pieces into the puzzle, or there can be a means to wait until all puzzle pieces have been inserted into the puzzle and then provide the scores at the end of the game to declare the winner. The calculation means for the scoring systems are identical what was described in the first embodiment, however, in this third embodiment, the scores are calculated through an electronic means. In this example of this embodiment, three scores will be displayed. One score in display 142 for weight change, one in display 144 for cholesterol level change and one in display 146 for blood pressure change. Additional electronic or digital displays can be added for more biometrics or parameters. Also, three electronic or digital displays can also have the means to display additional parameters. Additionally, only one digital display could be used which could have the means to display all parameters, one after each other or simultaneously. Again, typical biometrics or parameters for the example for this embodiment include changes in human weight, blood cholesterol level, blood glucose level, blood pressure, cancer prevention consumption, skin quality, renal disease prevention (protein level), endurance improvement, strength improvement and many other human biometrics, parameters, human conditions, human effects of consumption and human effects of exercise, however, this embodiment is not limited to these parameters or these biometrics. Examples other than human biometric measurements can be used for this embodiment. In addition, this embodiment is not limited to human biometrics and the like. This embodiment and all embodiments in this description can have a means to display parameters related to animal health, sports, dinosaurs, music, math, geographic or many other various game themes.

Figure 16:
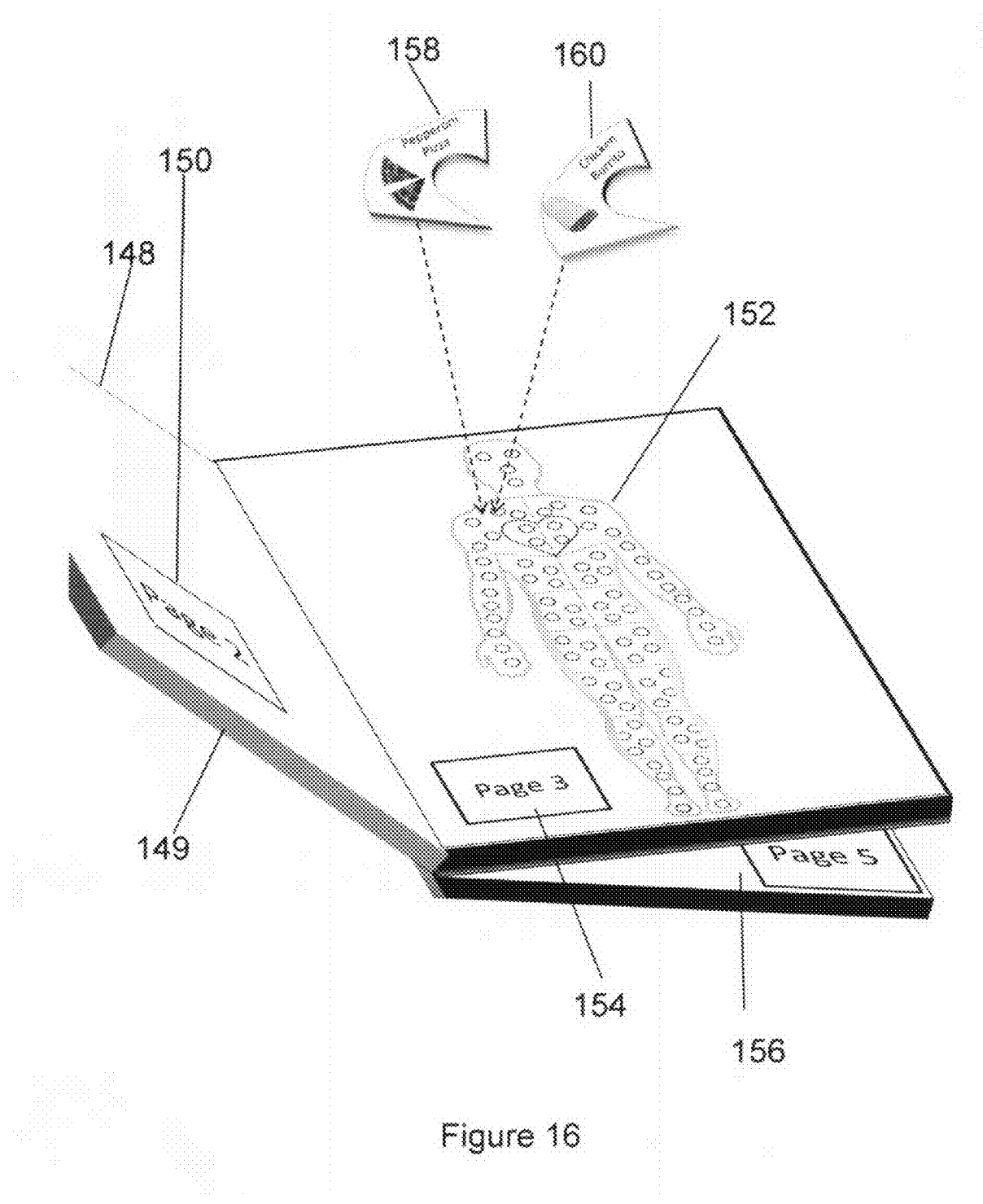
FIG. 16 is a puzzle game but in a book configuration, according to the present invention.

Fourth Embodiment—FIG. 16

FIG. 16 shows yet another example of a means to hold the puzzle pieces in place. In this case, FIG. 16 shows a book 148, with six pages. This book example of using a book design is non magnetic and non-metal and is made entirely out of paper or paper board or card board, however, it could be made out of any such material including but not limited to plastic, wood, foam, rubber or many other materials. In addition, the book could be magnetic or the puzzle pieces could be magnetic or metal or any combination of materials thereof. In this example, the book is made of paper board similar to what is commonly used for existing paperboard jigsaw puzzles that have been selling on the market for numerous years. Page 149 is the front page or page one of the book. Page two 150 of the book is open to show page three 154 of the book which is then followed by page four and page five 156 of the book. As shown in previous drawings and previous embodiments, the human shaped puzzle man, 152 is included on this example as shown on page three 154, of the book. Also shown on this page are two puzzle pieces 158 and 160 which are the left shoulder of the human shaped puzzle man 152. When the puzzle pieces 158 and 160 are placed in the human puzzle man 152, the puzzle pieces may fall out when page three is turned over to read the scores on the back of page four. In this case, to prevent the puzzle pieces from falling out, the player needs to close page two onto page three of the book thereby holding in the puzzle pieces. Once the pages are closed on each other, then the book can be opened to page four of the book to read the scores from the back of the puzzle board as described in the first and second embodiments, such as what is shown in FIG. 5. This embodiment is not limited to the system of using pages in a book to hold in the puzzle pieces when turning the puzzle board over. Many attachment systems can be provided, such as closing a book page on the puzzle pieces to hold them in place or attaching the puzzle pieces to the puzzle board using magnets, Velcro, a temporary adhesive, a mechanical latching or connecting system, placing a different type of cover or the puzzle pieces to hold them in place or any sort of means for attaching or holding one object onto another object.

Fifth Embodiment—FIG. 17

FIG. 17 illustrates a flow chart of the same functional game playing concept as described in previous embodiments except this fifth embodiment shows the flowchart of the game in a software version.

As shown in previous embodiments, the entire puzzle board game apparatus, including the scoring system on the back of the puzzle, can be a mechanical system as shown in first, second and fourth embodiments. This is illustrated in FIGS. 1 to 8 as well as in FIGS. 13, 14 and 16. The scoring system can also be an electronic version as shown in the third embodiment, which is illustrated in FIG. 15. Additionally, the same basic functions of the first four embodiments may also be transferred into a fully integrated software game used in a computing environment such as that shown in FIG. 18, computing environment 318. The computing environment 318 can be by means of common computer hardware or smart phone hardware or tablet hardware or any computing environment. All of the game play functions and features mentioned herein regarding the operation of the game in the first four embodiments can also be adapted to a software game using a variety of game software languages including but not limited to Assembly, C, C++, C#, Java, Eiffel, Smalltalk, Ada, Lua, Python and many others. Using software languages to develop this puzzle game into a software game based on all of the features described in these embodiments is a relatively well known existing technology and procedure. The flowchart for this fifth embodiment to develop a software means to translate the embodiments into software is shown in FIG. 17.

FIG. 17 shows the introduction 200 which explains the basics of the game and the purpose of the game for players who wish to read more detail. A main menu 202 which allows selections for configuration 206, game playing instructions 210, seeing the previously played high scores 212, escaping 214 or starting the game 204. Once the player decides to start the game, he or she has the option of playing the game locally 216 on his local computer, or escaping out of the game 218 or playing on line 220 on the internet, on line, with other players. If the player decides to play locally 240, then he must decide between a one player or a two player game 242. After deciding on the number of players, then the player must choose the biometric parameters 244 that he or she is playing for as shown in 246. Parameters are not limited to those shown in 246. As described in the previous embodiments, the game could be based on human biometrics parameters, but it could also be based on parameters related to a horse or to a sports team or to many other types of game themes.

If block 248, a one-player game is chosen, then the main playing field 250 is defined. In this example, the main playing field is a human puzzle 252. The software will then display the outline of a human puzzle man very similar to that shown in FIG. 1. Just as described in the previous embodiments for this particular example, each puzzle coordinate will have four choices of puzzle pieces. Since there are twenty puzzle coordinates, then there would be a total of eighty food, beverage and exercise choices for the human puzzle man. This embodiment is not limited to twenty coordinates or to four choices per coordinate or to a total of eighty choices or eighty puzzle pieces. Any number of coordinates can be used. Any number of choices per coordinate can be used. Any number of total choices can be used. For the example in this embodiment there will be twenty coordinates with four choices per coordinate and a total of eighty puzzle pieces or eighty choices. The eighty choices or eighty puzzle pieces, designated as 254, are then displayed to the player. The software will then allow the player to drag and drop the pieces into the human puzzle man as depicted by 256. Dragging and dropping software generated jigsaw puzzle pieces to make up a completed software jigsaw puzzle is a common software design and is available to be downloaded from the internet for free. Since the software is so common, the exact software code is not illustrated due to the fact that it is substantially available and has been so for many years. Once the software generated puzzle piece is dragged and dropped into the correct puzzle coordinate shown by 256, the score calculation takes place identical to the pulling data from data base tables 258 and performing a calculation as described in the previous embodiments regarding the data shown in FIGS. 9, 10, 11 and 12. Score values for the selected player are then tallied or added up per 260. After all of the puzzle pieces are dragged and dropped 256 into the virtual human puzzle man, the scores for the selected parameters are displayed as shown by 262. After the game scores are determined, the software will then access the biometric data in the Index database shown as 264. The index database is data derived from the spreadsheet figures shown in FIGS. 9 and 10 and the portion sizes shown in FIG. 12. Block 266 designates a simple lookup function that searches the database 264 and finds the data for the various biometric parameters that correlates to the puzzle score for each respective biometric parameter. Block 268 then depicts the next function which is to display the biometric parameters to the player. Block 270 then gives the player the option to save the game score. The player can then input his or her personal name, shown as block 308, and then have his game score recorded into the game memory under high score shown as block 310.

The players of the game also have the option to enter into a two player game as depicted by block 272. The sequence of the blocks in the flowchart for a two player game is basically identical to a one player game except for blocks 280 and 298.

If block 272, a two-player game is chosen, then the main playing field 274 is defined. In this example, the main playing field is two human puzzles shown as block 276. In this flowchart example, the game is limited to only two players, however, this embodiment can easily be expanded to a three or four player game. In addition, if the number of puzzle coordinates vary in quantity and the number of puzzle pieces that fit into each puzzle coordinate also vary in quantity, the puzzle game can easily changed to accommodate a plurality of players.

Once a two player game is selected, the software will then display the outline of two human puzzle men very similar to that shown in FIG. 1. Just as described for a one player game and in the previous embodiments for this particular example, each puzzle coordinate will have four choices of puzzle pieces. Since there are twenty puzzle coordinates, then there would be a total of eighty food, beverage and exercise choices for the human puzzle man. Again, this embodiment is not limited to twenty coordinates or to four choices per coordinate or to a total of eighty choices. Any number of coordinates can be used. Any number of choices per coordinate can be used. Any number of total choices can be used. For the example in this embodiment there will be twenty coordinates with four choices per coordinate and a total of eighty puzzle pieces or eighty choices. The eighty choices or eighty puzzle pieces designated as 278, are then displayed to the player. Block 280 requires that the two players must take one turn after another. In other words, only one puzzle piece can be placed into the puzzle for one turn, exactly as described in the first four embodiments. The software will then allow the players to drag and drop the pieces into their respective human puzzle man as depicted by 288. Dragging and dropping software generated jigsaw puzzle pieces to make up a completed software jigsaw puzzle is a common software design and is available to be downloaded from the internet for free. Since the software is so common, the exact software code is not illustrated in detail due to the fact that it is substantially available and has been so for many years. Once the software generated puzzle piece is dragged and dropped into the correct puzzle coordinate, the score calculation takes place identical to the pulling data from tables and performing a calculation as shown in block 290 and also as described in the previous embodiments regarding the data shown in FIGS. 9, 10, 11 and 12. Score values for the selected players are then tallied or summed per block 292. After all of the puzzle pieces are dragged and dropped into the virtual human puzzle man, the scores for the selected parameters are displayed as shown by 296. Scores for both players are allowed to seen by both players as shown in block 298. After the game scores are determined, the software will then access the biometric data in the index database shown as 300. The index database is data derived from the spreadsheet figures shown in FIGS. 9 and 10 and the portion sizes shown in FIG. 12. Block 302 designates a lookup function that searches the database and finds the data for the various biometric parameters that correlates to the puzzle score for each respective biometric parameter. Block 304 then depicts the next function which is to display the biometric parameters to the player. Block 306 then gives the players the option to save the game score. The players can then input their personal names, shown in block 308, and then have their game scores and all biometrics recorded into the game memory under block 310 which shows the high scores but also records all score history and biometric history for the players. After all of the players scores and the resulting puzzle man's biometric data have been recorded in block 310, the players can then input their personal biometric data into block 312. An example would be for a 30 year old woman to input her age, gender and her weight of 130 pounds. The input of personal biometric data is not limited to age, gender and weight, but it could be expanded to include blood pressure, cholesterol level, daily calories consumed, waist size and many other biometrics or effects. In addition, other inputs can be applied to this block 312 which include changing the portion sizes of the consumable items such as that shown in FIG. 12 and in many cases, such portion sizes are also shown on the puzzle game pieces. In addition, block 312 can provide input into changing the exercise habits in the puzzle game such as those shown on the puzzle pieces. Frequency information, such as that shown on FIG. 9, can also be part of the input data for block 132. The players would have the ability to adjust the frequency of the various items that make up the puzzle game. In addition, the duration period of the items in the frequency table in FIG. 9 can be recalculated or readjusted. The table on FIG. 9 is based on a duration period of 30 days, however this could be recalculated based on changing the duration period to any number of days, months or years. Different types of consumable items can also be input into block 312, which are not limited only to those shown on the played puzzle pieces. Any type of consumable item can be included on the input data. Consumable items can include food and drinks but can also include vitamins, minerals and a wide variety of food supplements. Even some limited environmental factors can also be input into block 312 such as elevation or altitude of the location where the player lives or how much sun a player is exposed to or many other environmental factors that may have an effect on the virtual human's heath or unhealthiness.

After the player or players have input their personal biometrics and other data into block 312, calculations are performed as shown in block 314. Block 314 provides a calculation means to convert the puzzle man from a virtual puzzle man with specific physical characteristics and life style habits to another virtual puzzle human with specific physical and life style habits that match the biometric inputs of the players. An example of how an operation of this calculation is performed is described in the "Operation" section of this document.

The calculation in block 314 is not limited to only the conversion of the data from one virtual puzzle human to another virtual puzzle human that matches or closely resembles the players, it can also apply directly to the individual players. If enough data and/or proper data is input into block 314, then the data that is output to block 316 can display a higher accuracy level of data that can be considered directly applicable to the players. Giving the player or players the ability to input their different choices into the virtual puzzle man via block 312 will result in an effect or a change to the virtual puzzle man. Given that the virtual puzzle man is a model of an average man in the United States, the players can make choices to see how the model of the puzzle man changes over a period of time. This change of the model over a period of time can be considered as a form of predictive modeling. The predictive modeling of a virtual puzzle man should be considered fairly accurate give that a component of the calculations are derived from valid references, such as Government references, published scientific data and other dependable sources.

This form of predictive modeling can also apply to each personal player of the game in these embodiments via the same method that it is used to predict the change in the human puzzle described herein.

In this embodiment and it all embodiments, more than a two player game can be provided. The number of players can be from one player to as many players as desired.

Block 220 gives the player the option to play the game on-line, on the internet. If the player chooses to play on-line, then a login can be provided as shown by 222. After entering a multiplayer lobby 224, the player can then invite one or more players as shown in block 226. Block 227 shows the response from a friend. If the response is a "yes" as shown by 228, then the players move on to the two player game sequence shown as block 230. If the response is a "no" as shown by 229, then the player reenters the multiplayer lobby 224. Again, if desired, more than a two player game can be provided. The number of players can be from one player to as many players as desired.

Once the players are in block 230, then the standard two player game sequence ensues identical to what was described starting with block 272, except this game is on-line, on the Internet. After the game is completed, the players can then view their achievements 232, which includes game scores and biometrics or parameter levels. The players can then login to their social media site shown by blocks 234 and 236 and then share their scores with their friends.

In comparison to other much more highly sophisticated software games available on the market today, this embodiment of a software puzzle game is would require a lower level of knowledge to program. There are many other software based jigsaw puzzle games that have been provided in the past in prior art. In fact many software based jigsaw puzzle games are available to download for free from the internet. The technology of placing software-generated jigsaw puzzle pieces into a jigsaw-generated puzzle framework is a common practice. What is missing from all prior art is that these embodiments described herein offer the players multiple scores for a single game play and having to make multiple choices for a single puzzle coordinate. Also the fact that an index is applied to the scores to relate to actual physical world parameters makes the feature of this embodiment novel and unobvious. In addition, the point that a calculation means can be applied to the game scores or the index, thereby relating to each individual player is another unobvious and novel feature.

Another feature of this embodiment is a combination of FIGS. 5 and 17. This feature involves using a smart phone "App" to take a photo of a completed puzzle score board, such as that shown in FIG. 5, and then have a smart phone automatically add up all of the player's scores. The App would then also provide the output of all of the biometrics or parameters of the puzzle man to the players. There are many known smart phone software applications or "Apps" that can perform optical character recognition (OCR). Different versions of OCR software exist on nearly all available smart phones. In addition, software based color recognition software of various versions are readily available and free to download from the Internet. OCR recognition software and color recognition software are common software technologies that are readily available and can be easily modified to accommodate this embodiment described for FIG. 5. In addition, software provided as shown in FIG. 17, blocks 258, 260, 262, 264, 266 and 268 can also be combined together with the OCR and color recognition software. The combination of these two software technologies would enable game players to quickly add up their scores for the puzzle man and also to quickly see the corresponding biometrics or parameters such as weight change, blood cholesterol level change, blood pressure change, blood glucose level change, skin quality change, antioxidant consumption level (cancer prevention), protein consumption (renal disease) and several other biometric parameters.

Figure 18:
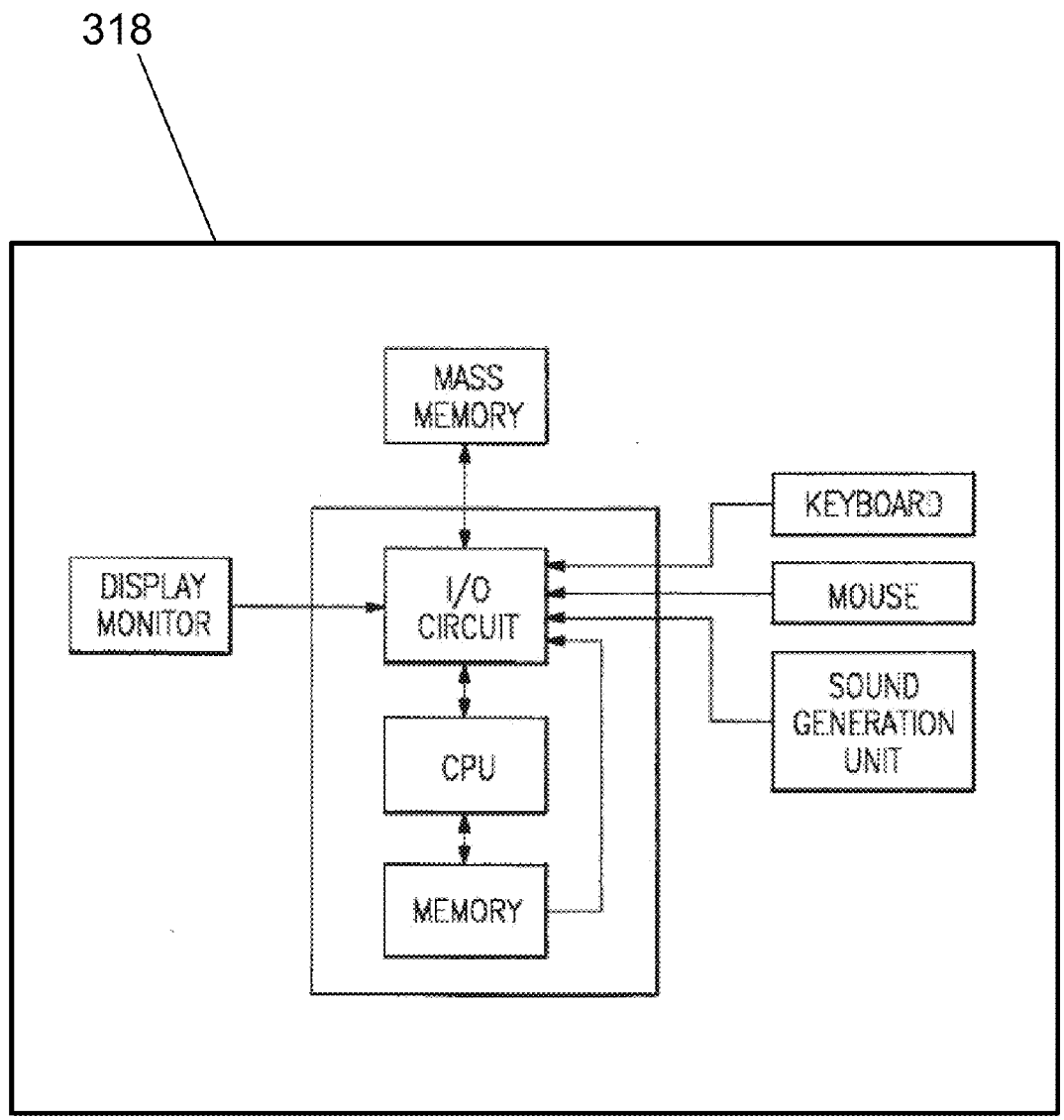
FIG. 18 is an example of computer hardware that makes up the computing environment to run software, according to the present invention.

FIG. 18 shows an example of the computing environment needed to run the software described in FIG. 17. FIG. 18 shows common hardware components of a common computer system. The computer environment needed to run the software described in FIG. 17 is not limited to the common hardware shown in FIG. 18. The computing environment could include smart phones, laptop computers, tablets or any sort of similar computer environment that provides a CPU like device and a display of various sorts as well as memory storage and other common components to run software similar to that show in FIG. 17.

Figure 19:
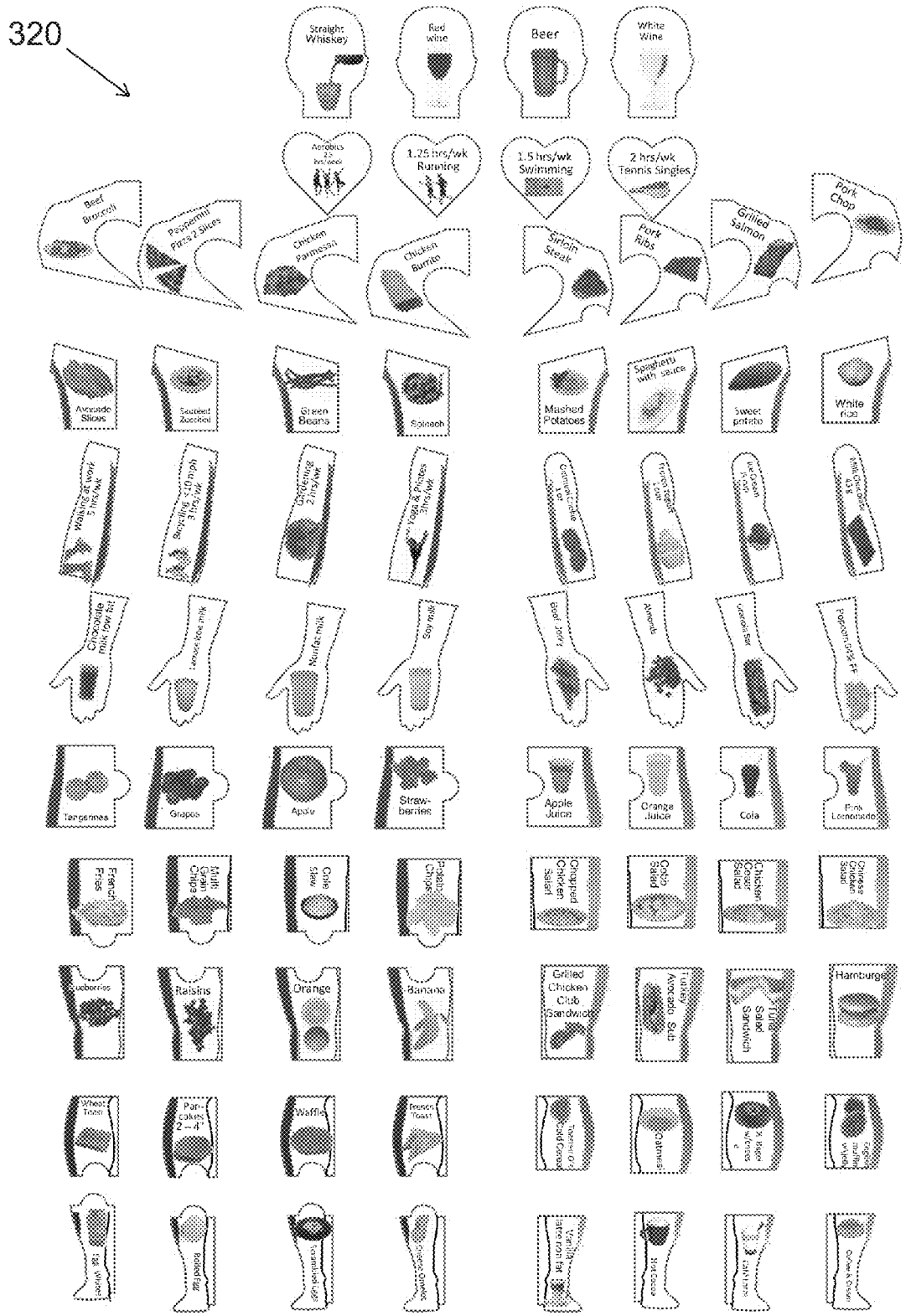
FIG. 19 shows examples of eighty puzzle pieces making up the human puzzle man, according to the present invention.

FIG. 19 shows examples of eighty puzzle pieces 320, which can be used in the examples shown for the embodiments herein. The eighty puzzle pieces 320 are designed to fill in the 20 coordinates of the jigsaw puzzle man shown on FIG. 1. Twenty of these eighty puzzle pieces are shown installed in the jigsaw puzzle man in FIG. 2. All of puzzle pieces could be included in all of these embodiments including the fifth embodiment which would use software-generated puzzle pieces.

Even though the example used in all of the described embodiments is that of a human shape, all of the described embodiments are not limited to that of a puzzle with a human shape. The shape of many other types of puzzles or different puzzle themes can be used such as the shape of a dinosaur or a shape of a geographical maps or a musical instrument or a math symbol or a football field, a horse or any sort of shape, even just a rectangle, a square or a circle. Likewise, the biometric parameters that make up the game, such as weight, cholesterol and blood pressure, could be substituted for many other parameters including those that would make up a different game theme. An example would be to make the puzzle in the shape of a horse and the front of the puzzle pieces could consist of horse food types, horse exercise types and different horse breeding types in order to have output parameters such as horse racing speed, horse endurance, coat quality, strength, size, demeanor, disease resistance, ruggedness, intelligence, longevity, trainability, coat color and many other such horse related factors. In addition, another example of this embodiment using a different shaped puzzle would be to shape the puzzle in the form of a football field with the puzzle coordinates being equal to the defensive and offensive player positions. The front of the puzzle pieces would be different players from many different football teams and the puzzle game players would have to decide which players to put into their puzzle board for defensive and offensive positions for their "football team". The output parameters would be various team statistics such as average game score, total rushing yards, total passing yards, total sacks and the like.

In addition, all of the embodiments are not limited to only one player or two players. All of the embodiments can be easily adapted to accommodate a plurality of players. The example given of the human puzzle man can easily accommodate up to four players with the design shown on the drawing figures. In the case of four players, each player would have their own game board, or players could team up on a single game board. In addition, the number of puzzle coordinates can be changed or increased and the number of choices or puzzle pieces for each puzzle coordinate can be changed or expanded to accommodate as many players as desired.

Operation

The object of the game is for each player to choose the best combination of puzzle pieces, such as those shown in FIG. 2, which will enable the player to have the best score to win the game. In the case of the example of a human shaped jigsaw puzzle game with all of the embodiments herein, the lowest score will be the best (winning) score. In the example of using a human shaped jigsaw game board, similar to what is shown in FIGS. 1, 2, 4, 5, 14, 15 and 16, this example will use two identical puzzle boards and have four puzzle pieces for each puzzle coordinate as depicted by the puzzle piece examples shown in FIG. 19. The embodiments herein are not limited to the lowest score, the design could be changed to the highest or the best score, but for purposes of this example, we will say that the player with the lowest score will be the winner. FIG. 19 shows examples of eighty puzzle pieces with four choices for each of twenty puzzle coordinates for this example. Since this example will use only two puzzle boards, then this would mean that in this example, there will be only two players, however, these embodiments are not limited to only two players or to two board or to eighty puzzle pieces or to twenty coordinates. Any number of players, playing boards, puzzle pieces, puzzle coordinates, puzzle scores and puzzle choices can be used. The embodiments can easily be changed to accommodate as many players as desired. For this example each of the two players will have their own playing board such as that shown in FIG. 16. The two man-shaped puzzle boards will have the identical shape and identically placed holes punched out in the back of each puzzle board and also have identically shaped puzzle coordinates and puzzle pieces. Due to the fact that five embodiments have previously been described, only the fourth embodiment which is shown in FIG. 16 will be used to describe the operation of the game and then the other embodiments will be compared to the fourth embodiment shown in FIG. 16.

As described above, each player will have their own puzzle board as shown in FIG. 16, but all players will share the same set of puzzle pieces. Puzzle outline 152 shows that there are 20 puzzle coordinates. This same puzzle outline 20 and the number of coordinates is also shown in FIG. 1. For the example of the human puzzle game for the embodiments herein, there will be four puzzle pieces per coordinate. Examples of twenty of the different types of puzzle pieces are as shown in FIG. 2. Examples of eighty puzzle pieces are shown in FIG. 19. At the very start of the game, each player will have a single, common pool of eighty puzzle pieces that they both must pull from the same pool which causes the players to be in competition with each other regarding which choices they make for each puzzle piece. Each player will take their turn choosing from the single pool of eighty puzzle pieces. Again, in this example, each puzzle piece will have a different type of food or drink or exercise image on each puzzle piece as shown in FIG. 19. Each player will "play" a puzzle piece by placing a single puzzle piece on their respective puzzle board coordinate by taking turns, one after the other. Again, the object of the game in this example is to have the lowest scores. By playing a puzzle piece, this simply means that the player will place the puzzle piece, such as 158, inside of the puzzle man 152 in its corresponding properly shaped puzzle coordinate. The best score, in this case, will result in choosing the best foods or the best drinks or the best exercises for the "man" in the puzzle. The better the score, the better the health and wellness of the puzzle man. In this case for this particular puzzle, the health categories that can be scored include three different biometrics which include 1) weight, 2) cholesterol level and 3) blood pressure as shown in FIG. 11. In this case, the best score will be the lowest score for each of the three biometric parameters, which is also indicated in FIG. 11. This embodiment is not limited to these three mentioned biometrics. Other biometrics or parameters can also be selected such as blood glucose level, cancer prevention, muscle mass building, endurance building, kidney health (renal disease), skin quality, joint inflammation or a pain, stomach inflammation or pain and many others.

The game players take turns choosing their respective twenty puzzle pieces. Only one puzzle piece can be "played" for each turn. Playing more than one piece during a turn is against the game rules. Each player chooses the best food to eat, the best drinks to drink and the best exercise to perform in order for their score to result in the lowest amount of calories (greatest amount of weight loss), lowest cholesterol level and lowest sodium intake (lowest blood pressure). What makes this puzzle game very novel and unobvious is that a single game played can result in more than just one score. In this example, a single game played will result in three separate scores, one for weight loss, one for blood cholesterol level change and one for blood pressure change. The player that chooses the healthiest puzzle pieces will result in the best score and win the game and beat the other players. The game begins with the players removing all of the puzzle pieces from the puzzle boards and placing the puzzle pieces face up on a table. Next, each player will take a turn choosing one of the puzzle pieces, one after the other, to place inside the proper puzzle coordinate in their respective puzzle board. The players choose the puzzle pieces until all coordinates in the puzzle are filled in on the front side of the two puzzle boards just as what is shown in FIG. 2. Once all puzzle coordinates are full with puzzle pieces, each player will close book page two 150 onto page three 154 as shown in FIG. 16. Closing the page on the puzzle pieces will attach or hold the puzzle pieces in place so that the puzzle pieces will not fall out when the puzzle board is turned over. The players will then open page 4 and page 5 shown as 156. Page four will be the back of the puzzle board, which is also shown as FIG. 5. This feature of closing the page is only needed if paper puzzle pieces are used or another non-magnetic material is used. If magnetic puzzle pieces are used or some other attachment method is needed, then the page two, shown as 150, does not need to be closed on page three, shown as 154.

Once the players have installed all twenty puzzle pieces and turned over the completed puzzle board and opened the book to pages four and five 156, they will then see the scores similar to that shown in FIG. 5. The players will also see different colors, such as 80 and 84, showing through all of the holes in FIG. 5. In this example, all of the score holes, such as those shown in FIG. 5, will have colors showing through the holes. All of the colors will come from the backside of all of the twenty puzzle pieces that each player placed into their respective puzzle man, 152. In this example, the colors on the back of the puzzle pieces will be shown will be red, green, yellow and black, similar to what is shown in FIG. 8.

Beside each hole is a number used as a score designator, such as that shown in FIG. 5, score 50, which shows a score of "2". Each hole in the puzzle score board is the associated score for each color that is showing through each hole. Each player will then add up the numbers for each individual color. The total of the numbers will represent the score for each biometrics, such as what is shown in FIG. 10, column 100 which shows a score for cholesterol, column 110 shows a score for blood pressure and column 118 shows a score for weight. Each color represents a different biometric. In this example, the biometric for cholesterol will have yellow colored dots. The biometric for blood pressure will have red colored dots. The biometric for weight will have green colored dots. The color of black will be no score or zero because it is not associated with any biometric parameter. Black dots are not added up or tallied. This is because in some instances, some of the consumable items do not affect certain biometrics or parameters. As an example, an apple has no cholesterol in it therefore, it would not have any yellow dots on the back of the puzzle piece that illustrates an apple on the front side. Instead, the apple would have a few black dots instead of yellow dots. These embodiments are not limited to the described colors. Any colors can be used for the scoring system. Once the game boards are turned over to the scoring side, each player would then add up the score numbers for each colored dot and compare to the other players. The players have the choice of using the best score or best scores or best 2 out of 3 scores for three biometrics. The ability to choose between one score or a plurality of scores is a novel and unobvious feature of this game and these embodiments. In this example, lowest score(s) win the game. This game is not limited to a lowest score to win the game. The game could be easily configured so that the highest score wins the game. This scoring system of using holes in the back of a jigsaw puzzle, as shown in FIG. 5, is a novel and unobvious feature not offered by prior art. In addition, another unique and novel feature of this embodiment is that after the scores are tallied up, each player can compare their scores to an "index" as shown in FIG. 11. The index will allow the players to see just exactly how their scores, or how their choices, change the physical condition of the puzzle man. In other words, the index will tell each player how much their scores caused the puzzle man to lose weight or gain weight. The index will tell the players how their choices changed the blood cholesterol level of the puzzle man. The index will also tell the players how their choices changed the blood pressure of the puzzle man. The index, FIG. 11, is a key feature of this game because it gives the player instant feedback regarding the quality of the player's choices. On the left side if the index, 122, is the player's score which then correlates to the right side of the index, 124, which shows the equivalent biometric, such as weight. The intent of this embodiment is to use this game to change people's behavior to make better choices in their nutrition and exercise habits thereby improving the general health of the population. It should be noted that this embodiment was specifically designed such that the front side of the puzzle board shown on page three 154 is highly subjective to the player, while at the same time, the back (scoring) side of the puzzle board, FIG. 5, is highly objective.

One of the novel and unobvious features of the described embodiments and the operation of this game is that you can utilize the index, FIG. 11, to compare how each player's choices in choosing the puzzle pieces, could impact their own personal body. This is done by converting the standardized characteristics of the puzzle man in the puzzle game to that of the physical characteristics of another standardized puzzle man that is almost identical to the characteristics of each player. In other words, it is a calculation process to convert the puzzle man in this example to another type of standardized human puzzle person, such as a 30 year old woman that weighs 130 pounds. In addition, with further data input, a calculation means can predict how the player's choices will impact the player's personal body to a much closer degree.

It is possible to calculate this due to the fact that the puzzle man's standardized physical body characteristics are considered as the standard basis for the index in FIG. 11. In this example, the physical puzzle man is shown in FIG. 1 and FIG. 2. The fixed physical characteristics of this particular example of a puzzle man, is a human male in the United States that weighs 195 pounds. He also sits at his desk at work 50% of the time. He also consumes about 2800 calories, 4400 milligrams of sodium and 379 milligrams of cholesterol each day.

Depending on each player's individual personal physical profile, their caloric needs will vary. For example, the puzzle man starts the game out at 195 pounds. The player chooses his foods on the puzzle pieces which reflect his intake over a period of 30 days. As a reference, the puzzle man's needs are based on the following calculations: 195 lbs, 5'10" and an activity level of 1.1.

Basal Energy Expenditure (BEE), which is the amount of energy required to maintain the body's normal metabolic activity, is calculated as follows:

$$\text{Men} = 66.5 + (13.75 \times \text{Wt in kg}) + (5.003 \times \text{Ht in cm}) - (\text{Age} \times 6.775)$$

$$\text{Women} = 655.1 + (9.563 \times \text{Wt in kg}) + (1.850 \times \text{Ht in cm}) - (\text{Age} \times 4.676)$$

Once BEE is calculated, additional factors such as stress, infection, physical activity, etc. are multiplied by BEE in order to obtain an individual's daily minimum caloric needs. The example puzzle man has an activity factor of 1.1, so therefore his daily estimated caloric need is 2083 calories. Prior to playing the game, his average daily intake is 2800 calories. As the player chooses foods for the virtual puzzle man, the puzzle man gains, maintains, or loses weight depending on whether he creates a caloric deficit or not. As a reference, one pound is equivalent to 3500 calories.

In order to have a customized, personal index outcome, an individual would first use a device such as a simple slide rule or a spreadsheet or a calculation means in one section to determine their true caloric need. Once the individual's caloric needs are calculated, their caloric needs are then compared to the reference standard, which is the puzzle man (his needs are 2083 calories per day). As an example, let's evaluate a 32-year old woman with the following biometrics: 130 lbs, 5'6" and an activity level of 1.3. Based on the above calculation, her estimated BEE is 1380 calories, and her activity factor is 1.3. Her daily need is 1794 calories, which is 289 calories less than the puzzle man. If the puzzle man's choices equate to 2083 calories each day for 30 days, he will maintain his weight of 195 lbs. If the same choices are applied to the sample woman above, she will gain approximately 2.5 lb because her caloric needs are less than the puzzle man.

Scenario based on the virtual puzzle man gaining 3 lbs of weight:

If the virtual puzzle man gained 3 lbs, what would happen to the woman outlined above? If the virtual puzzle man gained 3 lbs over a period of a month, his daily intake would be approximately 350 calories over his daily need (3 lbs×3500 calories÷30 days) and would equate to 2433 calories per day. If the woman made the exact same choices as the virtual puzzle man, she would have an excess caloric intake of 639 calories per day. This would cause her to gain 5.5 lbs (639 calories×30 days÷3500 calories).

Scenario based on the virtual puzzle man gaining 0 lbs of weight:

If the puzzle man maintained his weight of 195 lbs and did not gain or lose weight, what would happen to the woman outlined above? If the puzzle man consumed 2083 calories per day, his weight would remain the same. However, for the woman listed above, 2083 calories per day is an excess of 289 calories, which would result in a weight gain of 2.5 lbs (289 calories×30 days÷3500 calories).

Scenario based on the virtual puzzle man losing 3 lbs of weight:

If the virtual puzzle man lost 3 lbs over 30 days, what would happen to the woman outlined above? In order for the puzzle man to lose 3 lbs, he would have to reduce his daily intake by 350 calories, resulting in 1733 calories per day. If the woman outlined above ate 1733 calories per day, it would result in 0.5 lb weight loss for her.

These three scenarios demonstrate how the standardized index on FIG. 11 can be correlated directly to the player's own personal body. A simple customized slide rule, or a spreadsheet, or a software program or a smart phone App or any similar or other means can be used to perform this calculation. The ability of the players to relate their choices for the puzzle pieces directly to their own personal physical body is a novel feature of all of the described embodiments.

In the operation of this game, different playing strategies can be developed for a player to beat his or her opponent(s). Certain puzzle pieces may offer a greater weight or greater (or lesser) score as compared to other puzzle pieces. Multiple versions of the same puzzle game can be designed. An example of different versions would be that of a "virtual" puzzle man or a puzzle woman or a puzzle child, with each version having different sets of food, drinks and exercise choices. Other playing versions could be developed for people who have diabetes and they want to choose foods and drinks and exercises that will help to control their blood sugar level. The index for the game could be based on the blood sugar level change for the puzzle man. In addition, other versions can be developed for specific ethnic foods. Also versions can be developed for groups of people, such as people at a company with a group of employees, such as a company that has 5000 employees, that wish the puzzle game to have specific foods and drinks and exercise types that are tailored to their use and needs. This game also offers the optional feature that magnetic game puzzle pieces can also be placed on a person's refrigerator when the game is not in play. The intent with this is that after time, a player may want to use the puzzle pieces as a diet guide by placing the magnets with images of food and drinks and exercises on their refrigerator or other surface with the intent of using the magnetic puzzle pieces as a guide to help them with their eating habits and exercise habits. The magnetic puzzle pieces can even be placed on calendar to create an eating and exercise schedule. This game is not limited to magnetic puzzle pieces, but rather as described herein, the puzzle pieces can be made of any material and a combination of different materials.

Advantages:

From the description above, a number of advantages of some embodiments of my jigsaw puzzle game become evident:

A jigsaw puzzle game that can be played solitaire or with multiple players with each puzzle coordinate having multiple puzzle pieces that compete for the same puzzle coordinate.

Each puzzle piece has an indicator or indicia on the back of it that can indicate the player's score. An indicator can be a peg that sticks through the back of the puzzle, or a light that switches on, or a push-pull peg or an electronic means or a software means of indicating a score that is transmitted from the front of the puzzle board to the back of the puzzle board or to another easily visible area. In this example a very simple series of colors on the back of each puzzle piece is used and then matched up with small round holes or openings on the back of the puzzle board that can be used as a method to allow the game players to register a score for each player. The advantage is that the game scores are derived from the back of the puzzle piece.

A multiple scoring system for a single game play session is utilized which gives the players the choice of using just one score or using a plurality of scores to determine the winner. In this example, scores for cholesterol, blood pressure and weight change can be scored in a single game versus playing three separate games to obtain three separate scores.

An index is utilized for the subject matter or for each parameter of the puzzle game. In this example, an index for cholesterol level can be developed as well as an index for blood pressure and another index for body weight change.

Scores can be related to real-life parameters, such as general health, diabetes, renal disease and many other normal or abnormal health conditions and medical nutrition therapies.

A simple algorithm can also be applied to the individual player's personal biometric or other parameters so that the score of the game can be related personally to each player. As an example, a score of 43 for the game could equate to a weight loss of one pound on the index for the "virtual" puzzle man, but the algorithm could convert the weight loss for each specific player based on their individual physical body biometric characteristics. A slide rule or spread sheet or algorithm or software program can be easily developed to allow for this calculation based on the players personal biometric parameters such as, but not limited to, weight, sex, age, height and activity level.

The game can be highly educational and also can be designed to positively affect a person's behavior such as affecting the choices of their lifestyle as related to nutrition and fitness.

The puzzle game can easily be adapted into software. An example would be to have the game as an "app" on a smart phone or on a website or as a stand-alone game software programmed to run on any other type of device that can drive software. The entire puzzle game can be used with a similar scoring system with all of the features stated in these embodiments, except it will be driven as a software game with a very similar scoring system as described herein.

The entire puzzle game and all of the puzzle pieces can be easily customized to fit a certain group of people. An example is that is that the game can be customized according to the eating and physical activity levels of different groups of people, such as those with diabetes or those that only eat certain types of ethnic foods such as people in various countries around the world and with different languages and with different food types and the like.

CONCLUSIONS, RAMIFICATIONS AND SCOPE

As stated previously, this example of this embodiment is that of a human shape, however, the shape could be that of a dinosaur or a map of the United States or a musical instrument or a math symbol or a football helmet a horse or any sort of shape, even just a square or a circle. Likewise, the parameters that make up the game, such as weight, cholesterol and blood pressure, could be substituted for other parameters that make up different game themes. An example would be to make the puzzle in the shape of a horse and the front of the puzzle pieces could consist of horse food types, horse exercise types and horse breeding types in order to have output parameters such as speed, endurance, coat quality, strength, size, demeanor, disease resistance and other such horse related factors. In addition, another example of this embodiment using a different shaped puzzle would be to shape the puzzle in the form of a football field with the puzzle coordinates being equal to the defensive and offensive player positions. The front of the puzzle pieces would be different players from different teams and the game players would have to decide which players to put into their puzzle. The output parameters would be scores that match to an index related to various team statistics such as average game score, total rushing yards, total passing yards and the like.

The jigsaw game board and the puzzle pieces can also be manufactured out of a variety of materials. Materials can be composed a wide variety of common jigsaw materials such, but not limited to, various types of paper board or various types of wood or various types of plastics. In some cases, the materials can also be of various types of magnetic materials or various metals or various stones, ceramic, marble, glass and a wide variety of materials.

Multiple versions of the puzzle game can be provided. An example of different versions would be similar to the virtual puzzle man described in these embodiments would be to create multiple versions of the virtual puzzle man with different ages, different weights and many other different characteristics. In addition, multiple puzzle women can be provided. The same is also true for multiple puzzle children, with all of these and all embodiments with different versions having different sets of food, drink and exercise choices. Other playing versions can be provided for people who have diabetes and they want to learn to choose foods and drinks and exercises that will help to control their blood sugar level. The index for the game could be based on the blood sugar level for the puzzle man, or puzzle woman or puzzle child. In addition, other versions can be developed for specific ethnic foods. Also versions can be developed for groups of people, such as people at a company with a group of employees, such as a company that has 5000 employees and they wish that the puzzle game will have specific food and drinks and exercise types that are tailored or customized to their use and needs. This game also offers the feature that the magnetic game puzzle pieces can also be placed on a person's refrigerator when the game is not in play. The intent with this is that after time, a player may want to use the puzzle pieces as a diet guide by placing the magnets with images of food and drinks and exercises on their refrigerator or other surface with the intent of using the magnetic puzzle pieces as a guide to help them with their eating habits and exercise habits. The magnetic puzzle pieces can even be placed on calendar to create an eating and exercise schedule.

The index on FIG. 11 can be correlated directly to the player's own personal body characteristics or can be related to other parameters depending on the theme of the game. A simple customized slide rule or spreadsheet or a software program can be provided to perform this calculation. A spreadsheet can also perform this calculation or an "app" on a smart phone or many other means. The ability of the players to relate their choices for the puzzle pieces directly to their own personal physical body biometrics is a novel feature of all of the described embodiments.

While the invention herein disclosed has been described by means of specific embodiments and applications thereof, numerous modifications and variations could be made thereto by those skilled in the art without departing from the scope of the invention set forth in the claims.

What is claimed is:

1. A jigsaw puzzle board game comprising:
   (a) a game board comprising a composition of matter;
   (b) an outline of a human figure on said game board such that the outline of said human figure is flush with the front of said game board or physically recessed below the front of said game board or physically embedded within said game board;
   (c) a multiplicity of physical holes located within said outline of said human figure within said game board;
   (d) a multiplicity of physical puzzle pieces in the form of various human body parts that are properly shaped to fit within said outline of said human figure on said game board, (e) said multiplicity of puzzle pieces having a front side and a back side, at least two individual said puzzle pieces properly structurally shaped to fit within correspondingly shaped puzzle coordinates within said outline of said human figure;
   (f) at least one indicia of an outcome on the back side of each said puzzle piece where said indicia is structurally positioned to be displayed through said physical holes located within said outline of said human figure within said game board once said physical puzzle pieces are placed within said puzzle coordinates of said outline of a human figure
   (g) a scoring system that requires players to physically turnover said game board to the reverse side of said game board to allow said players to see said outcome of said indicia through said physical holes in said game board to determine the game scores for said players.

2. A puzzle board game comprising:
   (a) a game board comprising a composition of matter;
   (b) an outline of a human figure on said game board such that the outline of said human figure is flush with the front of said game board or physically recessed below the front of said game board or physically embedded within said game board;
   (c) a multiplicity of physical holes located within said outline of said human figure within said game board;
   (d) a multiplicity of physical puzzle pieces in the form of various human body parts that are properly shaped to fit within said outline of said human figure on said game board,
   (e) said multiplicity of puzzle pieces having a front side and a back side, at least two individual said puzzle pieces properly structurally shaped to fit within correspondingly shaped puzzle coordinates within said outline of said human figure;
   (f) at least one indicia of an outcome on the back side of each said puzzle piece where said indicia is structurally positioned to be displayed through said physical holes located within said outline of said human figure within said game board once said physical puzzle pieces are placed within said puzzle coordinates of said outline of a human figure;
   (g) a scoring system that requires players to physically turnover said game board to the reverse side of said game board to allow said players to see said outcome of said indicia through said physical holes in said game board to determine the game scores for said players.

3. The puzzle game of claim 2, wherein said game further comprises: a customized selection of said indicia on said puzzle pieces wherein said customized selection of indicia is selected for a certain person or certain groups of people.

4. The puzzle game of claim 2, wherein said game further comprises a scoring means for said scores to be displayed on a score sheet, wherein said score sheet is located separately from said game board.

5. The puzzle game of claim 2, wherein said game further includes a single index or multiple indices that can be used to translate or convert said scores for said players into a metric that relates to a subject matter of said game; and given that more than one said score can be provided for each said player for each play of said game, said various scores can then be applied to one or more said indices.

6. The puzzle game of claim 2, wherein said game further includes a calculation means for translating or converting said game scores into metrics that relate personally to an actual human figure by means of
    (a) having said puzzle game based on a set of standardized biometrics that make up a standardized virtual human figure;
    (b) providing for said puzzle game to allow each said player to change said set of standardized biometrics that make up said standardized virtual human figure; (c) wherein said set of standardized biometrics include weight, age, sex, height, physical activity, blood pressure, blood cholesterol level and other metrics.

7. A puzzle board game comprising:
    (a) a game board comprising a composition of matter;
    (b) an outline of an object on said game board such that the outline of said object is flush with the front of said game board or physically recessed below the front of said game board or physically embedded within said game board;
    (c) a multiplicity of physical holes located within said outline of said object being within said game board;
    (d) a multiplicity of physical puzzle pieces that are correspondingly shaped to fit within said outline of said object on said game board,
    (e) said multiplicity of puzzle pieces having a front and a back, at least two individual said puzzle pieces properly structurally shaped to fit within an associated and correspondingly shaped puzzle coordinate within said outline of said object wherein said puzzle coordinates have a multiplicity of different shapes;
    (f) at least one indicia of an outcome on the back side of each said puzzle piece where said indicia is structurally positioned to be displayed through said physical holes located within said outline of said object within said game board once said physical puzzle pieces are placed within said puzzle coordinates of said outline of said object;
    (g) a scoring system that requires players to physically turnover said game board to the reverse side of said game board to allow said players to see said outcome of said indicia through said physical holes in said game board to determine the game scores for said players.

8. The puzzle game of claim 7, wherein said game further comprises: a customized selection of said indicia on said puzzle pieces wherein said customized selection of indicia is selected for a certain person or certain groups of people.

9. The puzzle game of claim 7, wherein said game further comprises a scoring means for said scores to be displayed on a score sheet, wherein said score sheet is located separately from said game board.

10. The puzzle game of claim 7, wherein said game further includes a single index or multiple indices that can be used to translate or convert said scores for said players into a metric that relates to a subject matter of said game; and given that more than one said score can be provided for each said player for each play of said game, said various scores can then be applied to one or more said indices.

11. The puzzle game of claim 7, wherein said game further includes a calculation means for translating or converting said game scores into metrics that relates personally to an actual human figure by means of
    (a) having said puzzle game based on a set of standardized biometrics that make up a standardized virtual human figure;
    (b) providing for said puzzle game to allow each said player to change said set of standardized biometrics that make up said standardized virtual human figure; (c) wherein said set of standardized biometrics include weight, age, sex, height, physical activity, blood pressure, blood cholesterol level and other metrics.

* * * * *